(12) United States Patent
Ruoslahti et al.

(10) Patent No.: US 9,101,671 B2
(45) Date of Patent: *Aug. 11, 2015

(54) METHODS AND COMPOSITIONS RELATED TO CLOT BINDING COMPOUNDS

(75) Inventors: Erkki Ruoslahti, LaJolla, CA (US); Dmitri Simberg, LaJolla, CA (US)

(73) Assignee: Sanford-Burnham Medical Research Institute, La Jolla, CA (US)

(*) Notice: Subject to any disclaimer, the term of this patent is extended or adjusted under 35 U.S.C. 154(b) by 1290 days.

This patent is subject to a terminal disclaimer.

(21) Appl. No.: 11/967,509

(22) Filed: Dec. 31, 2007

(65) Prior Publication Data

US 2008/0305101 A1 Dec. 11, 2008

Related U.S. Application Data

(60) Provisional application No. 60/883,229, filed on Jan. 3, 2007, provisional application No. 60/883,890, filed on Jan. 8, 2007.

(51) Int. Cl.
| | | |
|---|---|---|
| A61K 39/00 | (2006.01) | |
| A61K 47/48 | (2006.01) | |
| A61K 49/18 | (2006.01) | |
| B82Y 5/00 | (2011.01) | |

(52) U.S. Cl.
CPC ..... *A61K 47/48861* (2013.01); *A61K 47/48238* (2013.01); *A61K 47/48815* (2013.01); *A61K 47/48884* (2013.01); *A61K 49/1863* (2013.01); *A61K 49/1866* (2013.01); *B82Y 5/00* (2013.01); *Y10T 428/2984* (2015.01)

(58) Field of Classification Search
None
See application file for complete search history.

(56) References Cited

U.S. PATENT DOCUMENTS

| | | | |
|---|---|---|---|
| 4,016,100 A | 4/1977 | Suzuki et al. | |
| 4,089,801 A | 5/1978 | Schneider et al. | |
| 4,235,871 A | 11/1980 | Papahadjopoulos et al. | |
| 4,342,566 A | 8/1982 | Theofilopoulos et al. | |
| 4,418,052 A | 11/1983 | Wong | |
| 4,485,054 A | 11/1984 | Mezei et al. | |
| 4,761,288 A | 8/1988 | Mezei et al. | |
| 4,816,567 A | 3/1989 | Cabilly et al. | |
| 4,853,228 A | 8/1989 | Wallach et al. | |
| 5,011,686 A | 4/1991 | Pang | |
| 5,013,497 A | 5/1991 | Yiournas et al. | |
| 5,024,829 A | 6/1991 | Berger et al. | |
| 5,084,824 A | 1/1992 | Lam et al. | |
| 5,288,514 A | 2/1994 | Ellman | |
| 5,362,831 A * | 11/1994 | Mongelli et al. | 526/304 |
| 5,449,754 A | 9/1995 | Nishioka | |
| 5,474,848 A | 12/1995 | Wallach | |
| 5,506,337 A | 4/1996 | Summerton et al. | |
| 5,539,083 A | 7/1996 | Cook et al. | |
| 5,545,568 A | 8/1996 | Ellman | |
| 5,556,762 A | 9/1996 | Pinilla et al. | |
| 5,565,324 A | 10/1996 | Still et al. | |
| 5,565,332 A | 10/1996 | Hoogenboom et al. | |
| 5,573,905 A | 11/1996 | Lerner et al. | |
| 5,618,825 A | 4/1997 | Baldwin et al. | |
| 5,619,680 A | 4/1997 | Berkovich et al. | |
| 5,627,210 A | 5/1997 | Valerio et al. | |
| 5,628,936 A | 5/1997 | Wallach | |
| 5,646,285 A | 7/1997 | Baindur et al. | |
| 5,653,996 A | 8/1997 | Hsu | |
| 5,663,046 A | 9/1997 | Baldwin et al. | |
| 5,670,326 A | 9/1997 | Beutel | |
| 5,677,195 A | 10/1997 | Winkler et al. | |
| 5,683,899 A | 11/1997 | Stuart | |
| 5,688,696 A | 11/1997 | Lebl | |
| 5,688,997 A | 11/1997 | Baldwin et al. | |
| 5,698,685 A | 12/1997 | Summerton et al. | |
| 5,712,146 A | 1/1998 | Khosla et al. | |
| 5,721,099 A | 2/1998 | Still et al. | |
| 5,721,367 A | 2/1998 | Kay et al. | |
| 5,723,598 A | 3/1998 | Lerner et al. | |
| 5,741,713 A | 4/1998 | Brown et al. | |
| 5,789,542 A | 8/1998 | McLaughlin et al. | |
| 5,792,431 A | 8/1998 | Moore et al. | |
| 5,792,742 A | 8/1998 | Gold et al. | |

(Continued)

FOREIGN PATENT DOCUMENTS

| | | |
|---|---|---|
| EP | 45665 | 2/1982 |
| WO | WO-9429348 | 12/1994 |
| WO | WO 96/33171 | 10/1996 |
| WO | WO-9964446 | 12/1999 |
| WO | WO 2005/016919 | 2/2005 |
| WO | WO 2005/046722 | 5/2005 |
| WO | WO 2005/039495 | 7/2005 |
| WO | WO 2007/108749 | 9/2007 |
| WO | WO 2008/057282 | 5/2008 |

OTHER PUBLICATIONS

Merriam-Webster Collegiate Dictionary definition for "plurality", tenth edition, Springfield, Massachusetts, 1997, p. 896.*
Cavaleri et al., Langmuir. Sep. 13, 2005;21(19):8758-64.*
Larson et al., Science. May 30, 2003;300(5624):1434-6.*
Abe K, et al. Regulation of vascular endothelial growth factor production and angiogenesis by the cytoplasmic tail of tissue factor. PNAS 96: 8663-8668 (1999).

(Continued)

*Primary Examiner* — Michael Szperka
(74) *Attorney, Agent, or Firm* — Jenkins, Wilson, Taylor & Hunt, P.A.

(57) ABSTRACT

Disclosed are compositions and methods related to clot binding compounds. For example, disclosed are conjugates comprising a surface molecule and a plurality of clot binding compounds. The clot binding compounds can selectively bind to clotted plasma protein. The conjugate can, for example, cause clotting and amplify the accumulation of the conjugate in tumors. In one example, the conjugate can comprise a sufficient number and composition of clot binding compounds such that the conjugate causes clotting and amplifies the accumulation of the conjugate in tumors. The disclosed targeting is useful for treatment of cancer and other diseases and disorders.

48 Claims, 9 Drawing Sheets

(56) References Cited

U.S. PATENT DOCUMENTS

| | | | |
|---|---|---|---|
| 5,804,440 A | 9/1998 | Burton | |
| 5,821,130 A | 10/1998 | Baldwin et al. | |
| 5,831,014 A | 11/1998 | Cook et al. | |
| 5,837,243 A | 11/1998 | Deo et al. | |
| 5,840,500 A | 11/1998 | Pei et al. | |
| 5,847,150 A | 12/1998 | Dorwald | |
| 5,856,107 A | 1/1999 | Ostresh et al. | |
| 5,856,496 A | 1/1999 | Fagnola et al. | |
| 5,859,190 A | 1/1999 | Meyer et al. | |
| 5,897,945 A | 4/1999 | Lieber et al. | |
| 5,916,899 A | 6/1999 | Kiely et al. | |
| 5,919,955 A | 7/1999 | Fancelli et al. | |
| 5,925,527 A | 7/1999 | Hayes et al. | |
| 5,939,598 A | 8/1999 | Kucherlapati et al. | |
| 5,942,387 A | 8/1999 | Hollinshead | |
| 5,948,696 A | 9/1999 | Dolle, III et al. | |
| 5,958,792 A | 9/1999 | Desai et al. | |
| 5,962,337 A | 10/1999 | Ohlmeyer | |
| 5,965,719 A | 10/1999 | Hindsgaul et al. | |
| 5,972,719 A | 10/1999 | Dolle, III et al. | |
| 5,976,894 A | 11/1999 | Dolle, III et al. | |
| 6,004,555 A | 12/1999 | Thorpe et al. | |
| 6,017,768 A | 1/2000 | Baldwin et al. | |
| 6,025,371 A | 2/2000 | Gordeev et al. | |
| 6,130,364 A | 10/2000 | Jakobovits et al. | |
| 6,180,377 B1 | 1/2001 | Morgan et al. | |
| 6,759,199 B2 | 7/2004 | Mirkin et al. | |
| 7,488,792 B2* | 2/2009 | Ruoslahti et al. | 530/300 |
| 2004/0009122 A1 | 1/2004 | Klaveness et al. | |
| 2005/0048063 A1* | 3/2005 | Ruoslahti et al. | 424/178.1 |
| 2005/0196343 A1* | 9/2005 | Reddy et al. | 424/9.322 |
| 2009/1003634 | 2/2009 | Ruoslahti | |
| 2011/0165064 A1 | 7/2011 | Ruoslahti | |

OTHER PUBLICATIONS

Akerman ME, et al. Nanocrystal targeting in vivo. PNAS 99: 12617-12621 (2002).
Allam et al. Cholera toxin triggers apoptosis in human lung cancer cell lines. Cancer Res 57: 2615-2618 (1997).
Alvarez-Bravo et al. Novel synthetic antimicrobial peptides effective against methicillin-resistant Staphylococcus aureus. Biochem J 302: 535-538 (1994).
Bangham, et al. Diffusion of univalent ions across the lamellae of swollen phospholipids. J Mol Biol 13: 238-252 (1965).
Barenholz et al. A new method for preparation of phospholipid vesicles (liposomes)—french press. FEBS Lett 99: 210-214 (1979).
Bessalle et al. All-D-magainin: chirality, antimicrobial activity and proteolytic resistance. FEBS 274: 151-155 (1990).
Blondelle and Houghten, Design of model amphipathic peptides having potent antimicrobial activities. Biochem 31: 12688-12694, 1992.
Blondelle and Houghten in Bristiol (Ed.) Annual Reports in Medicinal Chemistry pp. 159-168 Academic Press, San Diego, 1992.
Boccaccio C, et al. The MET oncogene drives a genetic programme linking cancer to haemostasis. Nature 434: 396-400 (2005).
Bode et al. Antibody-directed fibrinolysis. An antibody specific for both fibrin and tissue plasminogen activator. J Biol Chem 264(2): 944-948 (1989).
Borgstrom et al. Importance of VEGF for breast cancer angiogenesis in vivo: implications from intravital microscopy of combination treatments with an anti-VEGF neutralizing monoclonal antibody and doxorubicin. Anticancer Res 19: 4203-4214 (1999).
Boucher Y et al. Interstitial pressure gradients in tissue-isolated and subcutaneous tumors: implications for therapy. Cancer Res 50: 4478-4484 (1990).
Cai w, et al. Peptide-labeled near-infrared quantum dots for imaging tumor vasculature in living subjects. Nano Lett 6: 669-676 (2006).
Callow, et al. Thermodynamic modeling and cryomicroscopy of cell-size, unilamellar, and paucilamellar liposomes. Cryobiology 22(3): 251-267 (1985).

Chan, et al. Prospective randomized trial of docetaxel versus doxorubicin in patients with metastatic breast cancer. J Clin Oncol 17: 2341-2354 (1999).
Creighton, Proteins: Structures and Molecular Properties WH Freeman, New York (1984).
Crown J, The platinum agents: A role in breast cancer treatment? Seminars in Oncol 28: 28-37 (2001).
Davis et al. Isolation of angiopoietin-1, a ligand for the TIE2 receptor, by secretion-trap expression cloning. Cell 87: 1161-1169 (1996).
DeNardo SJ, et al. Development of tumor targeting bioprobes ((111)In-chimeric L6 monoclonal antibody nanoparticles) for alternating magnetic field cancer therapy. Clin Cancer Res 11: 7087s-7092s (2005).
De Roos A, et al. Myocardial infarct sizing and assessment of reperfusion by magnetic resonance imaging: a review. Int J Card Imaging 7:133 (1991).
Desai N, et al. Increased antitumor activity, intratumor paclitaxel concentrations, and endothelial cell transport of cremophor-free, albumin-bound paclitaxel, ABI-007, compared with cremophor-based paclitaxel. Clin Cancer Res 12: 1317-1324 (2006).
Dvorak HF, et al. Regulation of extravascular coagulation by microvascular permeability. Science 227: 1059-1061 (1985).
Ei-Sheikh A, et al. A selective tumor microvasculature thrombogen that targets a novel receptor complex in the tumor angiogenic microenvironment. Cancer Res 65: 11109-11117 (2005).
Fernandez-Urrusuno R, et al. Effect of polymeric nanoparticle administration on the clearance activity of the mononuclear phagocyte system in mice. J Biomed Mater Res 31: 401-408 (1996).
Fisher et al. Tamoxifen for prevention of breast cancer: report of the National Surgical Adjuvant Breast and Bowel Project P-1 Study. J Natl Cancer Inst 90: 1371-1388 (1998).
Fitzpatrick and Garnett, Design, synthesis and in vitro testing of methotrexate carrier conjugates linked via oligopeptide spacers. Anticancer Drug Des 10: 1-9 (1995).
Folkman, Addressing tumor blood vessels. Nature Biotechnology 15: 510 (1997).
Folkman and Shing, Angiogenesis. J Biol Chem 267: 10931-10934 (1992).
Gao X, et al. Quantum-dot nanocrystals for ultrasensitive biological labeling and multicolor optical encoding. J Biomed Opt 7: 532 (2002).
Goodman and Ro, Peptidomimetics for Drug Design, in "Burger's Medicinal Chemistry and Drug Discovery" vol. 1 (ed. ME Wolff; John Wiley & Sons 1995) pp. 803-861.
Gorbet MB, Sefton MV. Biomaterial-associated thrombosis: roles of coagulation factors, complement, platelets and leukocytes. Biomaterials 25: 5681-5703 (2004).
Hagedorn and Bikfalvi, Target molecules for anti-angiogenic therapy: from basic research to clinical trials. Crit Rev Oncol Hematol 34: 89-110 (2000).
Han M, et al. Quantum-dot-tagged microbeads for multiplexed optical coding of biomolecules. Nature Biotechnology 19: 631 (2001).
Hoffman JA, et al. Progressive vascular changes in a transgenic mouse model of squamous cell carcinoma. Cancer Cell 4: 383-391 (2003).
Holvoet et al. Thrombolytic profiles of clot-targeted plasminogen activators. Parameters determining potency and initial and maximal rates. Circulation, vol. 87, 1007-1016 (1993).
Homandberg et al. Heparin-binding fragments of fibronectin are potent inhibitors of endothelial cell growth. Am J Pathe 120: 327-332 (1985).
Homandberg et al. Heparin-binding fragments of fibronectin are potent inhibitors of endothelial cell growth: structure-function correlations. Biochim Biophys Acta 874: 61-71 (1986).
Huang X, et al. Tumor infarction in mice by antibody-directed targeting of tissue factor to tumor vasculature. Science 275: 547-550 (1997).
Hutchinson JN, Muller WJ. Transgenic mouse models of human breast cancer. Oncogene 19: 6130-6137 (2000).
Javadpour et al. De novo antimicrobial peptides with low mammalian cell toxicity. J Med Chem 39: 3107-3113 (1996).

(56) References Cited

OTHER PUBLICATIONS

Jung CW, Jacobs P. Physical and chemical properties of superparamagnetic iron oxide MR contrast agents: ferumoxides, ferumoxtran, ferumoxsil. Mang Reson Imaging 13: 661-674 (1995).
Jung CW. Surface properties of superparamagnetic iron oxide MR contrast agents: ferumoxides, ferumoxtran, ferumoxsil. Magn Reson Imaging 13: 675-691, 1995.
Kirsch et al. Anti-angiogenic treatment strategies for malignant brain tumors. J Neurooncol 50: 149-163 (2000).
Khandoga A, et al. Ultrafine particles exert prothrombotic but not inflammatory effects on the hepatic microcirculation in healthy mice in vivo. Circulation 109: 1320-1325 (2004).
Kim, et al. Solid core liposomes with encapsulated colloidal gold particles. Biochim et Biophys Acta 728: 339-348 (1983).
Kreitman and Pastan, Recombinant toxins containing human granulocyte-macrophage colonystimulating factor and either pseudomonas exotoxin or diphtheria toxin kill gastrointestinal cancer and leukemia cells. Blood 90: 252-259 (1997).
Laakkonen P, et al. A tumor-homing peptide with a targeting specificity related to lymphatic vessels. Nat Med 8: 751-755 (2002).
Laakkonen P, et al. Antitumor activity of a homing peptide that targets tumor lymphatics and tumor cells. PNAS 101: 9381-9386 (2004).
Lin Y, et al. Photonic pseudo-gap-based modification of photoluminescence from CdS nanocrystal satellites around polymer microspheres in a photonic crystal. Appl Phys Lett 81: 3134 (2002).
Maloy and Kari, Structure-activity studies on magainins and other host defense peptides. Biopolymers 37: 105-122 (1995).
Mancheno et al. A peptide of nine amino acid residues from alpha-sarcin cytotoxin is a membrane-perturbing structure. J Pept Res 51: 142-148 (1998).
Martin, et al. Cancer gene therapy by thyroid hormone-mediated expression of toxin genes. Cancer Res 60: 3218-3224 (2000).
Moghimi SM, et al. Long-circulating and target-specific nanoparticles: theory to practice. Pharmacol Rev 53: 283-318 (2001).
Moore A, et al. Uptake of dextran-coated monocrystalline iron oxides in tumor cells and macrophages. J Magn Reson Imaging 7: 1140-1145 (1997).
Morrison et al. Chimeric human antibody molecules: mouse antigen-binding domains with human constant region domains. PNAS 81: 6851-6855 (1984).
Oh P, et al. Subtractive proteomic mapping of the endothelial surface in lung and solid tumours for tissue-specific therapy. Nature 429: 629-635 (2004).
O'Reilly et al. Endostatin: an endogenous inhibitor of angiogenesis and tumor growth. Cell 88: 277-285 (1997).
O'Reilly et al. Antiangiogenic activity of the cleaved conformation of the serpin antithrombin. Science 285: 1926-1928 (1999).
Osborne and Coronado-Heinsohn, Targeting the epidermal growth factor receptor in breast cancer cell lines with a recombinant ligand fusion toxin (DAB389EGF). Cancer J Sci Am 2: 175 (1996).
Haik, et al. Development of Magnetic Device for Cell Separation. Mag & Magnetic Mater 194: 262 (1999).
Papahadjopoulos D, Miller M. Phospholipid model membranes. I. Structural characteristics of hydrated liquid crystals. Biochim et Biophys Acta 135: 624-638 (1967).
Paridaens et al. Paclitaxel versus doxorubicin as first-line single-agent chemotherapy for metastatic breast cancer: a European Organization for Research and Treatment of Cancer Randomized Study with cross-over. J Clin Oncol 18: 724 (2000).
Pasqualini R, Ruoslahti E. Organ targeting in vivo using phage display peptide libraries. Nature 380: 364-366 (1996).
Pilch J, et al. Peptides selected for binding to clotted plasma accumulate in tumor stroma and wounds. PNAS 103: 2800-2804 (2006).
Powers et al. Indium-111 platelet scintigraphy in cerebrovascular disease. Neurology 32: 938 (1982).
Radomski A, et al. Nanoparticle-induced platelet aggregation and vascular thrombosis. Br J Pharmacol 146: 882-93 (2005).
Ruoslahti E. Specialization of tumour vasculature. Ruoslahti E. Nat Rev Cancer 2: 83-90 (2002).
Saberwal et al. Cell-lytic and antibacterial peptides that act by perturbing the barrier function of membranes: facets of their conformational features, structure-function correlations and membrane-perturbing abilities. Biochim Biophys Acta 1197: 109-131 (1994).
Sinek J, et al. Two-dimensional chemotherapy simulations demonstrate fundamental transport and tumor response limitations involving nanoparticles. Biomed Microdevices 6: 297-309 (2004).
Souhami RL, et al. The effect of reticuloendothelial blockade on the blood clearance and tissue distribution of liposomes. Biochim Biophys Acta 674: 354-371 (1981).
Slavin J. Fibroblast growth factors: at the heart of angiogenesis. Cell Biol Int 19: 431-444 (1995).
Steiner, In "Angiogenesis: Key principles-Science, technology and medicine" pp. 449-454 (eds. Steiner et al.; Birkhauser Verlag, 1992).
Ratain, In: "Cancer: Principles and practice of oncology" 5th ed. Chap 19 (eds. DeVita, Jr. et al.; JP Lippincott 1997).
Suh TT, et al. Resolution of spontaneous bleeding events but failure of pregnancy in fibrinogen-deficient mice. Genes Dev 9: 2020-2033 (1995).
Suri et al. Requisite role of angiopoietin-1, a ligand for the TIE2 receptor, during embryonic angiogenesis. Cell 87: 1171-1180 (1996).
Thakur ML et al. Indium-LLL labeled platelets: studies on preparation and evaluation of in vitro and in vivo functions. Throm Res 9:345 (1976).
Van der Heyde HC, et al. Platelet depletion by anti-CD41 (alphallb) mAb injection early but not late in the course of disease protects against *Plasmodium berghei* pathogenesis by altering the levels of pathogenic cytokines. Blood 105: 1956-1963 (2005).
Van Rooijen N, Sanders A. Liposome mediated depletion of macrophages: mechanism of action, preparation of liposomes and applications. J Immunol Methods 174: 83-93 (1994).
Weissleder R, et al. Long-circulating Iron Oxides for MR Imaging. Advanced Drug Delivery Reviews 16: 321-334 (1995).
Weissleder R, et al. Superparamagnetic iron oxide: pharmacokinetics and toxicity. AJR Am J Roentgenol 152: 167-173 (1989).
White et al. Antibody-Targeted Immunotherapy for Treatment of Malignancy. Annu Rev Med 52: 125-141 (2001).
Agemy, et al., "Nanoparticle-induced vascular blockade in human prostrate cancer", Blood, 116(15):2847-56 (2010).
Beecken, et al., "Effect of antiangiogenic therapy on slowly growing, poorly vascularized tumors in mice", J. Natl. Cancer Inst., 93(5):382-87 (2001).
Bieker et al., "Infarction of tumor vessels by NGR': peptide-directed targeting of tissue factor: experimental results and first-in-man experience", Blood, vol. 113, No. 20, pp. 5019-5027 (2009).
Extended European Search Report corresponding to European Patent Application No. 07 870 130.7 dated May 8, 2013.
Fernandez-Urrusuno R, et al. Effect of polymeric nanoparticle administration on the clearance activity of the mononuclear phagocyte system in mice. J. Biomed. Mater. Res. 31: 401-408 (1996).
International Preliminary Report on Patentability corresponding to International Patent Application No. PCT/US2010/061302 dated Jun. 19, 2012.
International Search Report corresponding to International Patent Application No. PCT/US2010/061302 dated May 3, 2011.
International Search Report corresponding to PCT/US2007/89202 dated Sep. 9, 2008.
Notice of Allowance for U.S. Appl. No. 12/973,459 dated Aug. 11, 2014.
Office Action corresponding to Canadian Patent Application No. 2,674,378 dated Apr. 28, 2014.
Office Action corresponding to European Patent Application No. 10 803 685.6-1456 dated Apr. 17, 2013.
Office Action corresponding to Japanese Patent Application No. 2009-544907 dated Oct. 1, 2013. (with Translation).
Office Action corresponding to U.S. Appl. No. 12/973,459 dated Jul. 1, 2013.
Office Action corresponding to U.S. Appl. No. 12/973,459 dated Nov. 7, 2013.

(56) References Cited

OTHER PUBLICATIONS

Pai et al., "Microscopic flow visualization system for fluids in magnetic field", J. of Mag. & Magnetic Mater.,194:262-66 (1999).
Peters et al., PNAS, vol. 106, No. 24, 9815-9819 (2009).
Silva et al., Toxicological Sci., 85, 983-989 (2005).
Simberg et al., "Biomimetic amplification of nanoparticle homing to tumors", PNAS, vol. 104(3), 932-936 (2007).
Wang, et al., "Composite Photonic Crystals from Semiconductor Nanocrystal/Polyelectrolyte-Coated Colloidal Spheres", Chem. Mater., 15:2724-29 (2003).

* cited by examiner

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 1

Cys Arg Glu Lys Ala
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence; note =-
      synthetic construct

<400> SEQUENCE: 2

Cys Gly Leu Ile Ile Gln Lys Asn Glu Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence; note =-
      synthetic construct
```

```
<400> SEQUENCE: 3

Cys Asn Ala Gly Glu Ser Ser Lys Asn Cys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence; note =-
      synthetic construct
<220> FEATURE:
<221> NAME/KEY: VARIANT
<222> LOCATION: 2, 3, 4, 5, 6, 7, 8
<223> OTHER INFORMATION: Xaa = Any Amino Acid

<400> SEQUENCE: 4

Cys Xaa Xaa Xaa Xaa Xaa Xaa Xaa Cys
1               5
```

METHODS AND COMPOSITIONS RELATED TO CLOT BINDING COMPOUNDS

CROSS-REFERENCE TO RELATED APPLICATIONS

This application claims benefit of U.S. Provisional Application No. 60/883,229, filed Jan. 3, 2007, and to U.S. Provisional Application No. 60/883,890, filed Jan. 8, 2007, both herein incorporated by reference in their entirety.

STATEMENT REGARDING FEDERALLY SPONSORED RESEARCH

This invention was made with government support under CA119335 awarded by the National Institutes of Health (NIH). The government has certain rights in this invention.

FIELD OF THE INVENTION

The present invention relates generally to the fields of molecular medicine and cancer biology and, more specifically, to clot binding compounds that selectively home to tumor vasculature.

BACKGROUND OF THE INVENTION

A major hurdle to advances in treating cancer is the relative lack of agents that can selectively target the cancer while sparing normal tissue. For example, radiation therapy and surgery, which generally are localized treatments, can cause substantial damage to normal tissue in the treatment field, resulting in scarring and loss of normal tissue. Chemotherapy, in comparison, which generally is administered systemically, can cause substantial damage to organs such as the bone marrow, mucosae, skin and small intestine, which undergo rapid cell turnover and continuous cell division. As a result, undesirable side effects such as nausea, loss of hair and drop in blood cell count often occur when a cancer patient is treated intravenously with a chemotherapeutic drug. Such undesirable side effects can limit the amount of a drug that can be safely administered, thereby hampering survival rate and impacting the quality of patient life.

Nanomedicine is an emerging field that uses nanoparticles to facilitate the diagnosis and treatment of diseases. Notable early successes in the clinic include the use of superparamagnetic nanoparticles as a contrast agent in MRI and nanoparticle-based treatment systems (Desai 2006; Weissleder 1995). The first generation of nanoparticles used in tumor treatments rely on "leakiness" of tumor vessels for preferential accumulation in tumors; however, this enhanced permeability and retention (EPR) is not a constant feature of tumor vessels (Sinek 2004) and even when present, still leaves the nanoparticles to negotiate the high interstitial fluid pressure in tumors (Sinek 2004; Boucher 1990). An attractive alternative is to target nanoparticles to specific molecular receptors in the blood vessels because they are readily available for binding from the blood stream and because tumor vessels express a wealth of molecules that are not significantly expressed in the vessels of normal tissues (Hoffman 2003; Oh 2004; Ruoslahti 2002).

Specific targeting of nanoparticles to tumors has been accomplished in various experimental systems (DeNardo 2005; Akerman 2002; Cai 2006), but the efficiency of delivery is generally low. In nature, amplified homing is an important mechanism ensuring sufficient platelet accumulation at sites of vascular injury. It involves target binding, activation, platelet-platelet binding, and formation of a blood clot. What is needed in the art is a nanoparticle delivery system in which the particles amplify their own homing.

BRIEF SUMMARY OF THE INVENTION

Disclosed herein is a conjugate comprising a surface molecule and a plurality of clot binding compounds. The clot binding compounds can selectively bind to clotted plasma protein. The conjugate can cause clotting and amplify the accumulation of the conjugate in tumors. In one example, the conjugate can comprise a sufficient number and composition of clot binding compounds such that the conjugate causes clotting and amplifies the accumulation of the conjugate in tumors.

Sufficiency of the number and composition of clot binding compounds can be determined by assessing clotting and amplification of the accumulation of the conjugate in tumors in a non-human animal.

The conjugate can comprise a sufficient density and composition of clot binding compounds such that the conjugate causes clotting and amplifies the accumulation of the conjugate in tumors. Sufficiency of the density and composition of clot binding compounds can be determined by assessing clotting and amplification of the accumulation of the conjugate in tumors in a non-human animal.

A plurality of the clot binding compounds can each be independently selected from an amino acid segment comprising the amino acid sequence REK, a fibrin-binding peptide, a clot binding antibody, and a clot binding small organic molecule. A plurality of the clot binding compounds can each independently comprise an amino acid segment comprising the amino acid sequence REK.

The amino acid segments can each be independently selected from amino acid segments comprising the amino acid sequence CREKA (SEQ ID NO: 1) or a conservative variant thereof, amino acid segments comprising the amino acid sequence CREKA (SEQ ID NO:1), amino acid segments consisting of the amino acid sequence CREKA (SEQ ID NO:1), and amino acid segments consisting of the amino acid sequence REK. The amino acid segments can each independently comprise the amino acid sequence CREKA (SEQ ID NO: 1) or a conservative variant thereof.

The amino acid segments can also each independently comprise the amino acid sequence CREKA (SEQ ID NO:1). The amino acid segment can also consist of the amino acid sequence CREKA (SEQ ID NO:1). The amino acid segment can consist of the amino acid sequence REK.

A plurality of the clot binding compounds can each comprise a fibrin-binding peptide. The fibrin-binding peptides can independently be selected from the group consisting of fibrin binding proteins and fibrin-binding derivatives thereof. In another example, a plurality of the clot binding compounds can each comprise a clot binding antibody. Furthermore, a plurality of the clot binding compounds can each comprise a clot binding small organic molecule.

The surface molecule can be a nanoparticle, such as an iron oxide nanoparticle or an albumin nanoparticle. The surface molecule can also comprise a liposome, a microparticle, or a fluorocarbon microbubble. In one example, the surface molecule can be detectable. In another example, the surface molecule can be a therapeutic agent. An example of a therapeutic agent is Abraxane.

The conjugate can further comprise one or more moieties. For example, the moieties can be independently selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, and carbon-13. At least one of the moieties can be a therapeutic agent. Examples of therapeutic agents are paclitaxel and taxol. At least one of the moieties can be a detectable agent.

The conjugate can selectively home to clotted plasma protein. The conjugate can selectively home to tumor vasculature, wound sites, or both.

Disclosed herein is a method comprising administering to a subject the conjugate disclosed herein, wherein the conjugate selectively homes to clotted plasma protein, wherein the conjugate causes clotting and amplifies the accumulation of the conjugate at the site of the clotted plasma protein. The conjugate can selectively homes to tumor vasculature, wound sites, or both.

In one example, the conjugate can have a therapeutic effect. This can be achieved by the enhanced clot formation that occurs because of the conjugate. This effect can be enhanced by the delivery of a therapeutic agent to the site of the tumor or wound site.

The therapeutic effect can be a slowing in the increase of or a reduction of tumor burden. The therapeutic effect can also be a reduction or blocking of blood circulation in a tumor. The therapeutic effect can also be a reduction or cessation of bleeding at a wound site. The therapeutic effect can also be a decrease in the time for bleeding to stop in a wound site. The therapeutic effect can also comprises a reduction in inflammation, an increase in speed of wound healing, reduction in amounts of scar tissue, decrease in pain, decrease in swelling, decrease in necrosis, or a combination.

Furthermore, the clotting itself can have a therapeutic effect, as disclosed elsewhere herein. The subject can have one or more sites to be targeted, wherein the conjugate homes to one or more of the sites to be targeted. For example, the subject can have multiple tumors or sites of injury.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figure 1:
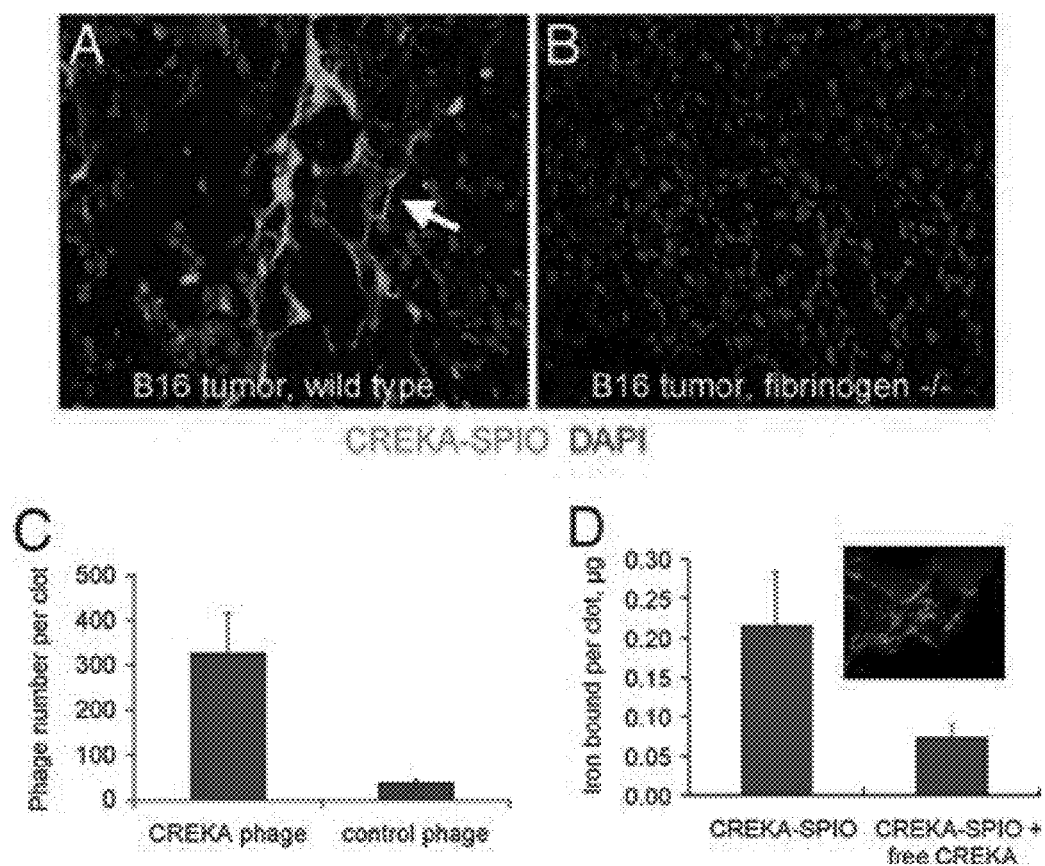
FIG. 1 shows tumor homing of CREKA pentapeptide. Fluorescein-conjugated CREKA peptide (200 μg per mouse) was injected into mice bearing syngeneic B16 melanoma tumors. Representative microscopic fields are shown to illustrate homing of fluorescein-CREKA to fibrin-like structures in tumors in wild type mice (A, arrow) and lack of homing in fibrinogen null mice (B). (C) The CREKA phage binds to clotted plasma proteins in the tube, while non-recombinant control phage shows little binding. (D) Dextran-coated iron oxide nanoparticles conjugated with fluorescein-CREKA bind to clotted plasma proteins, and the binding is inhibited by free CREKA peptide. The inset in (D) shows the microscopic appearance of the clot-bound CREKA-SPIO. Magnification: A-B, 200×; D, 600×.

The disclosed method and compositions can be understood more readily by reference to the following detailed description of particular embodiments and the Example included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Materials

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to a number of molecules including the peptide are discussed, specifically contemplated is each and every combination and permutation of the peptides and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed herein is a conjugate comprising a surface molecule and a plurality of clot binding compounds. The clot binding compounds can selectively bind to clotted plasma protein. The conjugate can cause clotting and amplify the accumulation of the conjugate in tumors. In some forms of the conjugate comprising a surface molecule and a plurality of clot binding compounds, the clot binding compounds selectively bind to clotted plasma protein and the conjugate causes clotting and amplifies the accumulation of the conjugate in tumors. Further disclosed are conjugates that not only home to tumors, but also amplify their own homing. The system is based on a clot binding compound that recognizes clotted plasma proteins and selectively homes to tumors, where it binds to vessel walls and tumor stroma. Surface molecules coupled with the clot binding compounds can accumulate in tumor vessels or at wound sites, where they induce additional local clotting, thereby producing new binding sites for more particles. The system mimics platelets, which also circulate freely but accumulate at a diseased site and amplify their own accumulation at that site. The clotting-based amplification greatly enhances tumor imaging, and a drug carrier function is also envisioned.

In developing new strategies for treating solid tumors, methods that involve targeting the vasculature of the tumor, rather than the tumor cells themselves, offer distinct advantages. Inducing a blockade of the blood flow through the tumor, e.g., through tumor vasculature specific fibrin formation, interferes with the influx and efflux processes in a tumor site, thus resulting in anti-tumor effect. Arresting the blood supply to a tumor can be accomplished through shifting the procoagulant-fibrinolytic balance in the tumor-associated vessels in favor of the coagulating (clotting) processes by specific exposure to clotting agents.

Conjugates comprising clot binding compounds are directed to the tumor cells themselves. There, they accumulate and induce additional clotting. A number of appropriate clot binding compounds have been identified that are specifically or preferentially expressed, localized, adsorbed to or inducible on the cells or in the environment of the tumor vasculature and/or stroma. These are discussed in more detail below.

A. Clot Binding Compounds

The clot binding compound can be any compound with the ability to interact with clots and/or components of clots such as clotted plasma proteins. The conjugate can comprise a sufficient number and composition of clot binding compounds such that the conjugate causes clotting and amplifies the accumulation of the conjugate in tumors and at the site of injury. In one example, sufficiency of the number and composition of clot binding compounds can be determined by assessing clotting and amplification of the accumulation of the conjugate in tumors in a non-human animal. Such methods are discussed in more detail below.

A plurality of the clot binding compounds can each be independently selected from, for example, an amino acid segment comprising the amino acid sequence REK, a fibrin-binding peptide, a peptide that binds clots and not fibrin (such as CGLIIQKNEC (CLT1, SEQ ID NO: 2) and CNAGESSKNC (CLT2, SEQ ID NO: 3)). a clot binding antibody, and a clot binding small organic molecule. A plurality of the clot binding compounds can each independently comprise an amino acid segment comprising the amino acid sequence REK.

The conjugate can comprise any number of clot binding compounds. By way of example, the conjugate can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more clot binding compounds. The conjugate can also comprise any number in between those numbers listed above.

The term "homing molecule" as used herein, means any molecule that selectively homes in vivo to specified target sites or tissues in preference to normal tissue. Similarly, the term "homing peptide" or "homing peptidomimetic" means a peptide that selectively homes in vivo to specified target sites or tissues in preference to normal tissue. It is understood that a homing molecule that selectively homes in vivo to, for example, tumors can home to all tumors or can exhibit preferential homing to one or a subset of tumor types.

By "selectively homes" is meant that, in vivo, the homing molecule binds preferentially to the target as compared to non-target. For example, the homing molecule can bind preferentially to clotted plasma of one or more tumors, wound tissue, or blood clots, as compared to non-tumoral tissue or non-wound tissue. Such a homing molecule can selectively home, for example, to tumors. Selective homing to, for example, tumors generally is characterized by at least a two-fold greater localization within tumors (or other target), as compared to several tissue types of non-tumor tissue. A homing molecule can be characterized by 5-fold, 10-fold, 20-fold or more preferential localization to tumors (or other target) as compared to several or many tissue types of non-tumoral tissue, or as compared to-most or all non-tumoral tissue. Thus, it is understood that, in some cases, a homing molecule homes, in part, to one or more normal organs in addition to homing to the target tissue. Selective homing can also be referred to as targeting.

1. Peptides

In one example, the clot binding compound can be a peptide or peptidomimetic. The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides can have any suitable length. The disclosed peptides can have, for example, a relatively short length of less than six, seven, eight, nine, ten, 12, 15, 20, 25, 30, 35 or 40 residues. The disclosed peptides also can be useful in the context of a significantly longer sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —$CH=CH$— (cis and trans), —$COCH_2$—, —$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$); Spatola et al. Life Sci 38:1243-1249 (1986) (—$CHH_2$—S); Hann J. Chem. Soc Perkin Trans. 1307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—$CH(OH)CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as β-alanine, γ-aminobutyric acid, and the like.

Also disclosed are bifunctional peptides, which contain the clot binding peptide fused to a second peptide having a separate function. Such bifunctional peptides have at least two functions conferred by different portions of the full-length molecule and can, for example, display anti-angiogenic activity or pro-apoptotic activity in addition to the ability to enhance clotting.

Also disclosed are isolated multivalent peptides that include at least two subsequences each independently containing a peptide (for example, the amino acid sequence SEQ ID NO: 1, or a conservative variant or peptidomimetic thereof). The multivalent peptide can have, for example, at least three, at least five or at least ten of such subsequences each independently containing a peptide. In particular embodiments, the multivalent peptide can have two, three, four, five, six, seven, eight, nine, ten, fifteen or twenty identical or non-identical subsequences. This is in addition to the multiple clot binding compounds that can comprise the conjugate. In a further embodiment, the multivalent peptide can contain identical subsequences, such as repeats of SEQ ID NO: 1. In a further embodiment, the multivalent peptide contains contiguous identical or non-identical subsequences, which are not separated by any intervening amino acids.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective interaction with a target of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α.-dialkylglycine or α-aminocycloalkane carboxylic acid; an $N^\alpha$—$C^\alpha$ cyclized amino acid; an $N^\alpha$.-methylated amino acid; a β- or γ-amino cycloalkane carboxylic acid; an α,β-unsaturated amino acid; a β,β-dimethyl or β-methyl amino acid; a β-substituted-2,3-methano amino acid; an N—$C^\epsilon$ or $C^\alpha$—$C^\Delta$ cyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., Acta Crystalloqr. Section B, 35:2331 (1979)). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively interacting with cancerous cells.

i. Homing Peptides

There are several examples in the art of peptides that home to clotted plasma protein. Examples include REK, peptides comprising REK, CREKA (SEQ ID NO: 1), and peptides comprising CREKA (SEQ ID NO: 1). The amino acid segments can also be independently selected from amino acid segments comprising the amino acid sequence CREKA (SEQ ID NO: 1) or a conservative variant thereof, amino acid segments comprising the amino acid sequence CREKA (SEQ ID NO:1), amino acid segments consisting of the amino acid sequence CREKA (SEQ ID NO:1), and amino acid segments consisting of the amino acid sequence REK. The amino acid segments can each independently comprise the amino acid sequence CREKA (SEQ ID NO: 1) or a conservative variant thereof.

The amino acid segments can also each independently comprise the amino acid sequence CREKA (SEQ ID NO:1). The amino acid segment can also consist of the amino acid sequence CREKA (SEQ ID NO:1). The amino acid segment can consist of the amino acid sequence REK.

ii. Fibrin Binding Peptides

The clot binding compound can also comprise a fibrin-binding peptide (FBP). Examples of fibrin-binding peptides are known in the art (Van Rooijen N, Sanders A (1994) J Immunol Methods 174: 83-93; Moghimi S M, Hunter A C, Murray J C (2001) Pharmacol Rev 53: 283-318; U.S. Pat. No. 5,792,742, all herein incorporated by reference in their entirety for their teaching concerning fibrin binding peptides).

iii. Other Clot-Binding Peptides

Clot-binding peptides can also bind to proteins other than fibrin. Example include peptides that bind to fibronectin that has become incorporated into a clot (Pilch et al., (2006) PNAS, 103: 2800-2804, hereby incorporated in its entirety for its teaching concerning clot binding peptides). An example of clot binding peptides include, but is not limited to, CGLIIQKNEC (CLT1, SEQ ID NO: 2) and CNAGESSKNC (CLT2, SEQ ID NO: 3). The amino acid segments can also be independently selected from amino acid segments comprising the amino acid sequence CLT1 or CLT2 (SEQ ID NOS: 2 or 3) or a conservative variant thereof, amino acid segments comprising the amino acid sequence CLT1 or CLT2 (SEQ ID NOS: 2 or 3), or amino acid segments consisting of the amino acid sequence CLT1 or CLT2 (SEQ ID NOS: 2 or 3). The amino acid segments can each independently comprise the amino acid sequence CLT1 or CLT2 (SEQ ID NOS: 2 or 3) or a conservative variant thereof.

The amino acid segments can also each independently comprise the amino acid sequence CLT1 or CLT2 (SEQ ID NOS: 2 or 3). The amino acid segment can also consist of the amino acid sequence CLT1 or CLT2 (SEQ ID NOS: 2 or 3).

2. Clot Binding Antibodies

The clot binding compound can comprise a clot binding antibody. Examples of clot binding antibodies are known in the art (Holvoet et al. Circulation, Vol 87, 1007-1016, 1993; Bode et al. J. Biol. Chem., Vol. 264, Issue 2, 944-948, January, 1989; Huang et al. Science 1997: Vol. 275. no. 5299, pp. 547-550, all of which are herein incorporated by reference in their entirety for their teaching concerning clot binding antibodies).

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to bind to, or otherwise interact with, clots. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222: 581, 1991).

Human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature*, 321:522-525 (1986), Riechmann et al., *Nature*, 332:323-327 (1988), Verhoeyen et al., *Science*, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

3. Small Organic Molecules

The clot binding compound can also be a small organic molecule. Small organic molecules that are capable of interacting with, or binding to, clots are known in the art. These molecules can also be identified by methods known in the art, such as combinatorial chemistry. Some forms of small organic molecules can be organic molecules having a molecular weight of less than 1000 Daltons.

Combinatorial chemistry includes but is not limited to all methods for isolating small molecules that are capable of interacting with a clot, molecules associated with a clot such as fibrin or fibronectin, or clotted plasma protein, for example. One synthesizes a large pool of molecules and subjects that complex mixture to some selection and enrichment process, such as the detection of an interaction with clots.

Using methodology well known to those of skill in the art, in combination with various combinatorial libraries, one can isolate and characterize those small molecules which bind to or interact with the desired target. The relative binding affinity of these compounds can be compared and optimum compounds identified using competitive binding studies, which are well known to those of skill in the art. For example, a competitive binding study using CREKA (SEQ ID NO: 1) can be used.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in iterative processes.

Libraries of small organic molecules generally comprise at least 2 organic compounds, often at least about 25, 100 500 different organic compounds, more usually at least about 1000 different organic compounds, preferably at least about 2500 different organic compounds, more preferably at least about 5000 different organic compounds and most preferably at least about 10,000 or more different organic compounds. Libraries may be selected or constructed such that each individual molecule of the library may be spatially separated from the other molecules of the library (e.g., each member of the library is present in a separate microtiter well) or two or more members of the library may be combined if methods for deconvolution are readily available. The methods by which the library of organic compounds are prepared will not be critical to the invention.

B. Surface Molecules

The surface molecules, alternatively referred to as a surface particles, disclosed herein can be conjugated with clot binding compounds in such a way that the conjugate is delivered to a clot, where it can accumulate and cause further clotting. The surface molecule can be any substance that can be used with the clot binding compounds, and is not restricted by size or substance. Examples include, but are not limited to, nanoparticles (such as iron oxide nanoparticles or albumin nanoparticles), liposomes, small organic molecules, microparticles, or microbubbles, such as fluorocarbon microbubbles. The term surface molecule is used to identify a component of the disclosed conjugate but is not intended to be limiting. In particular, the disclosed surface molecules are not limited to substances, compounds, compositions, particles or other materials composed of a single molecule. Rather, the disclosed surface molecules are any substance(s), compound(s), composition(s), particle(s) and/or other material(s) that can be conjugated with a plurality of clot binding compounds such that at least some of the clot binding compounds are presented and/or accessible on the surface of the surface molecule. A variety of examples of suitable surface molecules are described and disclosed herein.

The surface molecule can be detectable, or can be a therapeutic agent such as Abraxane™. The section below, which discusses moieties that can be detectable or therapeutic, also applies to the surface molecule.

1. Nanoparticles, Microparticles, and Microbubbles

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohoms, nano-onions, nanorods, nanoropes and quantum dots. A nanoparticle can produce a detectable signal, for example, through absorption and/or emission of photons (including radio frequency and visible photons) and plasmon resonance.

Microspheres (or microbubbles) can also be used with the methods disclosed herein. Microspheres containing chromophores have been utilized in an extensive variety of applications, including photonic crystals, biological labeling, and flow visualization in microfluidic channels. See, for example, Y. Lin, et al., Appl. Phys Lett. 2002, 81, 3134; D. Wang, et al., Chem. Mater. 2003, 15, 2724; X. Gao, et al., J. Biomed. Opt. 2002, 7, 532; M. Han, et al., Nature Biotechnology. 2001, 19, 631; V. M. Pai, et al., Mag. & Magnetic Mater. 1999, 194, 262, each of which is incorporated by reference in its entirety. Both the photostability of the chromophores and the monodispersity of the microspheres can be important.

Nanoparticles, such as, for example, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

2. Liposomes

"Liposome" as the term is used herein refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 µm. These MLVs were first described by Bangham, et al., J Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 µm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. 1, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 µm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

C. Moieties

The conjugate disclosed herein can further comprise one or more moieties. For example, the moieties can be independently selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, and carbon-13. At least one of the moieties can be a therapeutic agent. Examples of therapeutic agents are paclitaxel and taxol. At least one of the moieties can be a detectable agent.

As used herein, the term "moiety" is used broadly to mean a physical, chemical, or biological material that generally imparts a biologically useful function to a linked or conjugated molecule. As disclosed herein, the properties of the moiety can also be found in a surface molecule, or both the surface molecule and the moiety can share one of the traits disclosed herein. For example, the surface molecule can comprise a detectable agent, while the moiety can comprise a therapeutic agent. This also applies for the clot binding compound, which can also comprise one or more of the properties of moieties as disclosed herein. The description of therapeutic and detectable agents which follows is intended to apply to any of moieties, surface molecules, or clot binding compounds. Thus, for example, moieties can be conjugated to, coupled to, or can be part of the disclosed surface molecules, clot binding compounds, or conjugates of surface molecules and clot binding compounds.

A moiety can be any natural or nonnatural material including, without limitation, a biological material, such as a cell, phage or other virus; an organic chemical such as a small molecule; a radionuclide; a nucleic acid molecule or oligonucleotide; a polypeptide; or a peptide. Useful moieties include, but are not limited to, therapeutic agents such as cancer chemotherapeutic agents, cytotoxic agents, pro-apoptotic agents, and anti-angiogenic agents; detectable labels and imaging agents; and tags or other insoluble supports. Useful moieties further include, without limitation, phage and other viruses, cells, liposomes, polymeric matrices, non-polymeric matrices or particles such as gold particles, microdevices and nanodevices, and nano-scale semiconductor materials. These and other moieties known in the art can be components of a conjugate.

1. Therapeutic Agents

The moiety can be a therapeutic agent. As used herein, the term "therapeutic agent" means a molecule which has one or more biological activities in a normal or pathologic tissue. A variety of therapeutic agents can be used as a moiety.

In some embodiments, the therapeutic agent can be a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

Taxanes are chemotherapeutic agents useful with the conjugates disclosed herein. Useful taxanes include, without limitation, docetaxel (Taxotere; Aventis Pharmaceuticals, Inc.; Parsippany, N.J.) and paclitaxel (Taxol; Bristol-Myers Squibb; Princeton, N.J.). See, for example, Chan et al., J. Clin. Oncol. 17:2341-2354 (1999), and Paridaens et al., J. Clin. Oncol. 18:724 (2000).

A cancer chemotherapeutic agent useful with the conjugates disclosed herein also can be an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, Nature Biotechnology 15:510 (1997); Steiner, In "Angiogenesis: Key principles-Science, technology and medicine," pp. 449-454 (eds. Steiner et al.; Birkhauser Verlag, 1992)), which can contribute to its effectiveness in treating cancer.

An alkylating agent such as melphalan or chlorambucil also can be a useful cancer chemotherapeutic agent. Similarly, a vinca alkaloid such as vindesine, vinblastine or vinorelbine; or an antimetabolite such as 5-fluorouracil, 5-fluorouridine or a derivative thereof can be a useful cancer chemotherapeutic agent.

A platinum agent also can be a useful cancer chemotherapeutic agent. Such a platinum agent can be, for example, cisplatin or carboplatin as described, for example, in Crown, Seminars in Oncol. 28:28-37 (2001). Other useful cancer chemotherapeutic agents include, without limitation, methotrexate, mitomycin-C, adriamycin, ifosfamide and ansamycins.

A cancer chemotherapeutic agent useful for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a conjugate for treatment of breast cancer (Fisher et al., J. Natl. Cancer Instit. 90:1371-1388 (1998)).

The therapeutic agent can be an antibody such as a humanized monoclonal antibody. As an example, the anti-epidermal growth factor receptor 2 (HER2) antibody, trastuzumab (Herceptin; Genentech, South San Francisco, Calif.) can be a therapeutic agent useful for treating HER2/neu overexpressing breast cancers (White et al., Annu. Rev. Med. 52:125-141 (2001)).

Useful therapeutic agents also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed conjugates and methods.

In one embodiment, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β, granulocyte macrophage colony stimulating factor (GM-CSF), granulocyte colony stimulating factor (G-CSF), interferon .alpha. (IFN-α); interferon .gamma. (IFN-γ), interleukin-1 (IL-1), interleukin-2 (IL-2), interleukin-3 (IL-3), interleukin-4 (IL-4), interleukin-6 (IL- 6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, *Pseudomonas* exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art (see below). It is understood that these and other polypeptides with biological activity can be a "therapeutic polypeptide."

A therapeutic agent can also be an anti-angiogenic agent. As used herein, the term "anti-angiogenic agent" means a molecule that reduces or prevents angiogenesis, which is the growth and development of blood vessels. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, anti-sense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Vascular endothelial growth factor (VEGF) has been shown to be important for angiogenesis in many types of cancer, including breast cancer angiogenesis in vivo (Borgstrom et al., Anticancer Res. 19:4213-4214 (1999)). The biological effects of VEGF include stimulation of endothelial cell proliferation, survival, migration and tube formation, and regulation of vascular permeability. An anti-angiogenic agent can be, for example, an inhibitor or neutralizing antibody that reduces the expression or signaling of VEGF or another angiogenic factor, for example, an anti-VEGF neutralizing monoclonal antibody (Borgstrom et al., supra, 1999). An anti-angiogenic agent also can inhibit another angiogenic factor such as a member of the fibroblast growth factor family such as FGF-1 (acidic), FGF-2 (basic), FGF-4 or FGF-5 (Slavin et al., Cell Biol. Int. 19:431-444 (1995); Folkman and Shing, J. Biol. Chem. 267:10931-10934 (1992)) or an angiogenic factor such as angiopoietin-1, a factor that signals through the endothelial cell-specific Tie2 receptor tyrosine kinase (Davis et al., Cell 87:1161-1169 (1996); and Suri et al., Cell 87:1171-1180 (1996)), or the receptor of one of these angiogenic factors. It is understood that a variety of mechanisms can act to inhibit activity of an angiogenic factor including, without limitation, direct inhibition of receptor binding, indirect inhibition by reducing secretion of the angiogenic factor into the extracellular space, or inhibition of expression, function or signaling of the angiogenic factor.

A variety of other molecules also can function as anti-angiogenic agents including, without limitation, angiostatin; a kringle peptide of angiostatin; endostatin; anastellin, heparin-binding fragments of fibronectin; modified forms of antithrombin; collagenase inhibitors; basement membrane turnover inhibitors; angiostatic steroids; platelet factor 4 and fragments and peptides thereof, thrombospondin and fragments and peptides thereof; and doxorubicin (O'Reilly et al., Cell 79:315-328 (1994)); O'Reilly et al., Cell 88:277-285 (1997); Homandberg et al., Am. J. Path. 120:327-332 (1985); Homandberg et-al., Biochim. Biophys. Acta 874:61-71 (1986); and O'Reilly et al., Science 285:1926-1928 (1999)). Commercially available anti-angiogenic agents include, for example, angiostatin, endostatin, metastatin and 2ME2 (EntreMed; Rockville, Md.); anti-VEGF antibodies such as Avastin (Genentech; South San Francisco, Calif.); and VEGFR-2 inhibitors such as SU5416, a small molecule inhibitor of VEGFR-2 (SUGEN; South San Francisco, Calif.) and SU6668 (SUGEN), a small molecule inhibitor of VEGFR-2, platelet derived growth factor and fibroblast growth factor I receptor. It is understood that these and other anti-angiogenic agents can be prepared by routine methods and are encompassed by the term "anti-angiogenic agent" as used herein.

The conjugates disclosed herein can also be used at a site of inflammation or injury. Moieties useful for this purpose can include therapeutic agents belonging to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue. Examples of useful therapeutic agents include but are not limited to steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, and integrins.

Useful therapeutic agents also can be antimicrobial peptides. This can be particularly useful to target a wound or other infected sites. Thus, for example, also disclosed are moieties comprising an antimicrobial peptide, where the conjugate is selectively internalized and exhibits a high toxicity to the targeted area. Useful antimicrobial peptides can have low mammalian cell toxicity when not incorporated into the conjugate. As used herein, the term "antimicrobial peptide" means a naturally occurring or synthetic peptide having antimicrobial activity, which is the ability to kill or slow the growth of one or more microbes. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli, Pseudomonas aeruginosa* or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic .alpha.-helical structure (see U.S. Pat. No. 5,789,542; Javadpour et al., J. Med. Chem. 39:3107-3113 (1996); and Blondelle and Houghten, Biochem. 31: 12688-12694 (1992)). An antimicrobial peptide also can be, for example, a β-strand/sheet-forming peptide as described in Mancheno et al., J. Peptide Res. 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, Biopolymers 37:105-122 (1995); Alvarez-Bravo et al., Biochem. J. 302:535-538 (1994); Bessalle et al., FEBS 274:-151-155 (1990.); and Blondelle and Houghten in Bristol (Ed.), Annual Reports in Medicinal Chemistry pages 159-168 Academic Press, San Diego). An antimicrobial peptide also can be an analog of a natural peptide, especially one that retains or enhances amphipathicity (see below).

An antimicrobial peptide incorporated into the conjugate disclosed herein can have low mammalian cell toxicity when linked to the conjugate. Mammalian cell toxicity readily can be assessed using routine assays. As an example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 µM for lytic activity, preferably concentrations greater than 200, 300, 500 or 1000 µM.

In one embodiment, disclosed are conjugates in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art.

An antimicrobial peptide that induces significant mitochondrial swelling at, for example, 50 µM, 40 µ.M, 30 µM, 20 µM, 10 µM, or less, is considered a peptide that promotes disruption of mitochondrial membranes.

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, Proteins: Structures and Molecular Properties W. H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., Biochim. Biophys. Acta 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., Biopolymers 37:105-122 (1995)).

As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic .alpha.-helical structure generally has an equivalent number of polar and nonpolar residues within the amphipathic domain and a sufficient number of basic residues to give the peptide an overall positive charge at neutral pH (Saberwal et al., Biochim. Biophys. Acta 1197: 109-131 (1994)). One skilled in the art understands that helix-promoting amino acids such as leucine and alanine can be advantageously included in an antimicrobial peptide (see, for example, Creighton, supra, 1984). Synthetic, antimicrobial peptides having an amphipathic α-helical structure are known in the art, for example, as described in U.S. Pat. No. 5,789,542 to McLaughlin and Becker.

It is understood by one skilled in the art of medicinal oncology that these and other agents are useful therapeutic agents, which can be used separately or together in the disclosed compositions and methods. Thus, it is understood that the conjugates disclosed herein can contain one or more of such therapeutic agents and that additional components can be included as part of the composition, if desired. As a non-limiting example, it can be desirable in some cases to utilize an oligopeptide spacer between the clot binding compound and the therapeutic agent (Fitzpatrick and Garnett, Anticancer Drug Des. 10:1-9 (1995)).

Other useful agents include thrombolytics, aspirin, anticoagulants, painkillers and tranquilizers, beta-blockers, ace-inhibitors, nitrates, rhythm-stabilizing drugs, and diuretics. Agents that limit damage to the heart work best if given within a few hours of the heart attack. Thrombolytic agents that break up blood clots and enable oxygen-rich blood to flow through the blocked artery increase the patient's chance of survival if given as soon as possible after the heart attack. Thrombolytics given within a few hours after a heart attack are the most effective. Injected intravenously, these include anisoylated plasminogen streptokinase activator complex (APSAC) or anistreplase, recombinant tissue-type plasminogen activator (r-tPA), and streptokinase. The disclosed compounds can use any of these or similar agents.

2. Detectable Agents

The moiety in the disclosed conjugates can also be a detectable agent. A variety of detectable agents are useful in the disclosed methods. As used herein, the term "detectable agent" refers to any molecule which can be detected. Useful detectable agents include compounds and molecules that can be administered in vivo and subsequently detected. Detectable agents useful in the disclosed compositions and methods include yet are not limited to radiolabels and fluorescent molecules. The detectable agent can be, for example, any molecule that facilitates detection, either directly or indirectly, preferably by a non-invasive and/or in vivo visualization technique. For example, a detectable agent can be detectable by any known imaging techniques, including, for example, a radiological technique, a magnetic resonance technique, or an ultrasound technique. Detectable agents can include, for example, a contrasting agent, e.g., where the contrasting agent is ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, Gd can be used as a non-radioactive detectable agent in certain embodiments.

Other examples of detectable agents include molecules which emit or can be caused to emit detectable radiation (e.g., fluorescence excitation, radioactive decay, spin resonance excitation, etc.), molecules which affect local electromagnetic fields (e.g., magnetic, ferromagnetic, ferromagnetic, paramagnetic, and/or superparamagnetic species), molecules which absorb or scatter radiation energy (e.g., chromophores and/or fluorophores), quantum dots, heavy elements and/or compounds thereof. See, e.g., detectable agents described in U.S. Publication No. 2004/0009122. Other examples of detectable agents include a proton-emitting molecules, a radiopaque molecules, and/or a radioactive molecules, such as a radionuclide like Tc-99m and/or Xe-13. Such molecules can be used as a radiopharmaceutical. In still other embodiments, the disclosed compositions can comprise one or more different types of detectable agents, including any combination of the detectable agents disclosed herein.

Useful fluorescent moieties include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Particularly useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio. Fluorescent probes and there use are also described in Handbook of Fluorescent Probes and Research Products by Richard P. Haugland.

Further examples of radioactive detectable agents include gamma emitters, e.g., the gamma emitters In-111, I-125 and I-131, Rhenium-186 and 188, and Br-77 (see. e.g., Thakur, M. L. et al., Throm Res. Vol. 9 pg. 345 (1976); Powers et al., Neurology Vol. 32 pg. 938 (1982); and U.S. Pat. No. 5,011, 686); positron emitters, such as Cu-64, C-11, and O-15, as well as Co-57, Cu-67, Ga-67, Ga-68, Ru-97, Tc-99m, In-113m, Hg-197, Au-198, and Pb-203. Other radioactive detectable agents can include, for example tritium, C-14 and/or thallium, as well as Rh-105, I-123, Nd-147, Pm-151, Sm-153, Gd-159, Tb-161, Er-171 and/or Tl-201.

The use of Technitium-99m (Tc-99m) is preferable and has been described in other applications, for example, see U.S. Pat. No. 4,418,052 and U.S. Pat. No. 5,024,829. Tc-99m is a gamma emitter with single photon energy of 140 keV and a half-life of about 6 hours, and can readily be obtained from a Mo-99/Tc-99 generator.

In some embodiments, compositions comprising a radioactive detectable agent can be prepared by coupling a targeting moiety with radioisotopes suitable for detection. Coupling can occur via a chelating agent such as diethylenetriaminepentaacetic acid (DTPA), 4,7,10-tetraazacyclododecane-N—,N',N'',N'''-tetraacetic acid (DOTA) and/or metallothionein, any of which can be covalently attached to the targeting moiety. In some embodiments, an aqueous mixture of technetium-99m, a reducing agent, and a water-soluble ligand can be prepared and then allowed to react with a disclosed targeting moiety. Such methods are known in the art, see e.g., International Publication No. WO 99/64446. In some embodiments, compositions comprising radioactive iodine, can be prepared using an exchange reaction. For example, exchange of hot iodine for cold iodine is well known in the art. Alternatively, a radio-iodine labeled compound can be prepared from the corresponding bromo compound via a tributylstannyl intermediate.

Magnetic detectable agents include paramagnetic contrasting agents, e.g., gadolinium diethylenetriaminepentaacetic acid, e.g., used with magnetic resonance imaging (MRI) (see, e.g., De Roos, A. et al., Int. J. Card. Imaging Vol. 7 pg. 133 (1991)). Some preferred embodiments use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70. Suitable ions include, but are not limited to, chromium(III), manganese(II), iron(II), iron(III), cobalt(II), nickel(II), copper(II), praseodymium(III), neodymium(III), samarium(III) and ytterbium(III), as well as gadolinium(III), terbium(III), dysoprosium(III), holmium(III), and erbium(III). Some preferred embodiments use atoms with strong magnetic moments, e.g., gadolinium(III).

In some embodiments, compositions comprising magnetic detectable agents can be prepared by coupling a targeting moiety with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the targeting moiety in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (e.g., hydroxides, carbonates and/or bicarbonates of sodium, potassium and/or lithium), organic bases, and/or basic amino acids can be used to neutralize acidic groups, e.g., to facilitate isolation or purification of the composition.

In preferred embodiments, the detectable agent can be coupled to the conjugate in such a way so as not to interfere with the ability of the clot binding compound to interact with the clotting site. In some embodiments, the detectable agent can be chemically bound to the clot binding compound. In some embodiments, the detectable agent can be chemically bound to a moiety that is itself chemically bound to the clot binding compound, indirectly linking the imaging and targeting moieties.

D. Pharmaceutical Compositions and Carriers

The disclosed compositions can be administered in vivo either alone or in a pharmaceutically acceptable carrier. By "pharmaceutically acceptable" is meant a material that is not biologically or otherwise undesirable, i.e., the material can be administered to a subject, along with the conjugate disclosed herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

1. Pharmaceutically Acceptable Carriers

The conjugates disclosed herein can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

E. Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed conjugates, peptides, etc., are also disclosed. Thus, the products produced using the molecular modeling approaches that involve the disclosed conjugates are also considered herein disclosed.

Thus, one way to isolate molecules that bind a molecule of choice is through rational design. This can be achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol._Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

F. Compositions with Similar Functions

It is understood that the compositions disclosed herein have certain functions, such as binding to clots or enhancing clot formation. Disclosed herein are certain structural requirements for performing the disclosed functions, and it is understood that there are a variety of structures which can perform the same function which are related to the disclosed structures, and that these structures will ultimately achieve the same result, for example stimulation or inhibition.

G. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits can include the conjugates disclosed herein.

H. Mixtures

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

I. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated.

J. Computer Readable Media

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

K. Peptide Synthesis

The compositions disclosed herein and the compositions necessary to perform the disclosed methods can be made using any method known to those of skill in the art for that particular reagent or compound unless otherwise specifically noted.

One method of producing the disclosed proteins, such as SEQ ID NO:1, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Methods

Disclosed herein is a method comprising administering to a subject the conjugate disclosed herein. The conjugate can selectively home to clotted plasma protein. The conjugate can cause clotting and amplify the accumulation of the conjugate at the site of the clotted plasma protein. Some forms of the method comprise administering to a subject the conjugate disclosed herein, wherein the conjugate selectively homes to clotted plasma protein, wherein the conjugate causes clotting and amplifies the accumulation of the conjugate at the site of the clotted plasma protein. The conjugate can selectively homes to tumor vasculature, wound sites, or both.

In one example, the conjugate can have a therapeutic effect. This can be achieved by the enhanced clot formation that occurs because of the conjugate. This effect can be enhanced by the delivery of a therapeutic agent to the site of the tumor or wound site.

The therapeutic effect can be a slowing in the increase of or a reduction of tumor burden. This slowing in the increase of, or reduction in the tumor burden, can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement in the increase of, or reduction in the tumor burden of, compared with a non-treated tumor, or a tumor treated by a different method.

The therapeutic effect can also be a reduction or blocking of blood circulation in a tumor. This reduction or blocking of blood circulation in a tumor, can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement in effective blocking of blood circulation in a tumor, compared with a non-treated tumor, or a tumor treated by a different method.

The therapeutic effect can also be a reduction or cessation of bleeding at a wound site. This reduction or cessation of bleeding at a wound site can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more reduction or cessation of bleeding at a wound site compared to a non-treated wound, or a wound treated with a different method.

The therapeutic effect can also be a decrease in the time for bleeding to stop in a wound site. This reduction or cessation of bleeding at a wound site can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more decrease in the time for bleeding to stop at a wound site compared to a non-treated wound, or a wound treated with a different method.

The therapeutic effect can also comprises a reduction in inflammation, an increase in speed of wound healing, reduction in amounts of scar tissue, decrease in pain, decrease in swelling, decrease in necrosis, or a combination. This effect can be a 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement compared to a non-treated subject, or a subject treated with a different method.

Furthermore, the clotting itself can have a therapeutic effect, as disclosed elsewhere herein. The subject can have one or more sites to be targeted, wherein the conjugate homes to one or more of the sites to be targeted. For example, the subject can have multiple tumors or sites of injury.

The disclosed conjugates can be used to treat any disease where uncontrolled cellular proliferation occurs such as cancers. A non-limiting list of different types of cancers can be as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

The disclosed conjugates can also be administered following decoy particle pretreatment to reduce uptake of the conjugates by reticuloendothelial system (RES) tissues. Such decoy particle pretreatment can prolong the blood half-life of the particles and increases tumor targeting.

A. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Biomimetic Amplification of Nanoparticle Homing to Tumors

Nanoparticle-based diagnostics and therapeutics are useful because multiple functions can be built into the particles. One such function is an ability to home to specific sites in the body. Described herein are biomimetic particles that not only home to tumors, but also amplify their own homing. The system is based on a peptide that recognizes clotted plasma proteins and selectively homes to tumors, where it binds to vessel walls and tumor stroma. Iron oxide nanoparticles and liposomes coated with this tumor-homing peptide accumulate in tumor vessels, where they induce additional local clotting, thereby producing new binding sites for more particles. The system mimics platelets, which also circulate freely but accumulate at a diseased site and amplify their own accumulation at that site. The clotting-based amplification greatly enhances tumor imaging, and the addition of a drug carrier function to the particles can also be used.

i. Results

CREKA Peptide.

Figure 5:
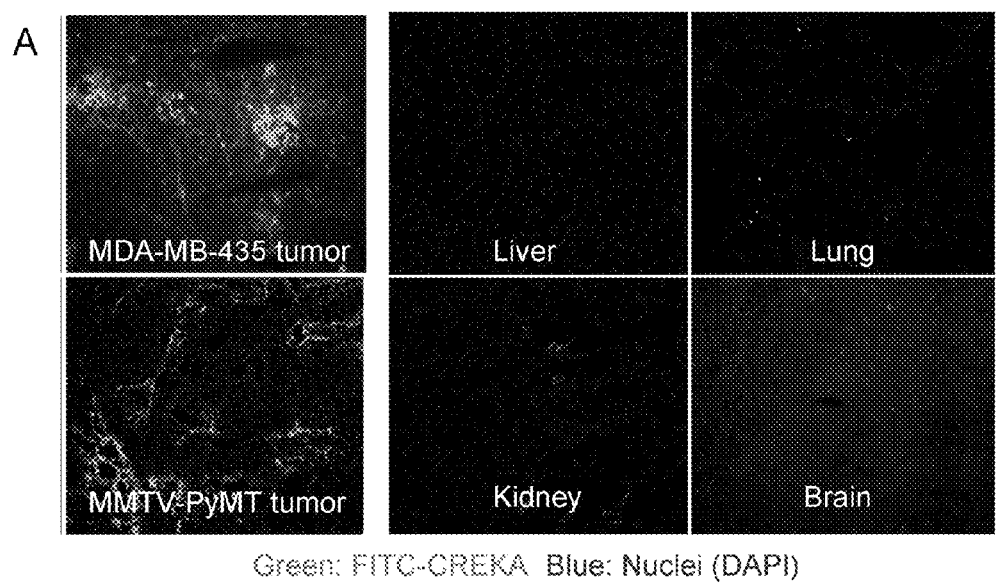
FIG. 5 shows tumor homing of CREKA peptide. (A). Balb/c nude mice bearing MDA-MB-435 human breast cancer xenograft tumors or transgenic MMTV PyMT mice with breast tumors were intravenously injected with 0.1 mg of fluorescein-CREKA. The animals were sacrificed by perfusion 24 hours post-injection and tissue sections were examined by fluorescent microscopy. Right panel, control organs of MDA-MB 435 tumor mice. Magnification 200×. (B). Whole animal imaging of MDA-MB-435 tumor mouse injected 6 hours earlier with 30 μg of Alexa Fluor 647-labeled CREKA. Maestro imaging system (Cambridge Research Inc., Woburn, Mass.) was used to acquire and process the image. The arrow points to the tumor and the arrowhead to the urinary bladder. Note that the peptide is excreted into the urine and does not accumulate in the liver.
Figure 5:
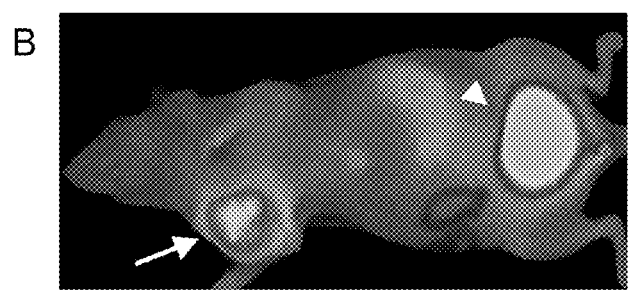

A tumor-homing peptide was used to construct targeted nanoparticles. This peptide was identified by in vivo screening of phage-displayed peptide libraries (Hoffman 2003; Pasqualini 1996) for tumor homing in tumor-bearing MMTV-PyMT transgenic breast cancer mice (Hutchinson 2000). The most frequently represented peptide sequence in the selected phage preparation was CREKA (cys-arg-glu-lys-ala; SEQ ID NO:1). The CREKA peptide was synthesized with a fluorescent dye attached to the N-terminus and the in vivo distribution of the peptide was studied in tumor-bearing mice. Intravenously injected CREKA peptide was readily detectable in the PyMT tumors, and in MDA-MB-435 human breast cancer xenografts, minutes to hours after the injection. The peptide formed a distinct meshwork in the tumor stroma (FIG. 5), and it also highlighted the blood vessels in the tumors. The CREKA peptide was essentially undetectable in normal tissues. In agreement with the microscopy results, whole body imaging using CREKA peptide labeled with the fluorescent dye Alexa 647 revealed peptide accumulation in the breast cancer xenografts, and in the bladder, reflecting elimination of excess peptide into the urine (FIG. 5B).

Tumors contain a meshwork of clotted plasma proteins in the tumor stroma and the walls of vessels, but no such meshwork is detectable in normal tissues (Dvorak 1985; Abe 1999; Pilch 2006). The mesh-like pattern produced by the CREKA peptide in tumors prompted the study of whether clotted plasma proteins can be the target of this peptide. The peptide was tested in fibrinogen knockout mice, which lack the fibrin meshwork in their tumors. Like previously identified clot-binding peptides (Pilch 2006), intravenously injected CREKA peptide failed to accumulate in B16F1 melanomas grown in the fibrinogen null mice, but formed a brightly fluorescent meshwork in B16F1 tumors grown in normal littermates of the null mice (FIGS. 1A and B). In agreement with this result, the CREKA phage, but not the control insert-less phage, bound to clotted plasma proteins in vitro (FIG. 1C). These results establish CREKA as a clot-binding peptide. Its structure makes it an attractive peptide to use in nanoparticle targeting because, unlike other clot-binding peptides, which are cyclic 10 amino-acid peptides (Pilch 2006), CREKA is linear and contains only 5 amino acids. Moreover, the sulfhydryl group of the single cysteine residue is not required to provide binding activity and can be used to couple the peptide to other moieties.

Peptide-Coated Nanoparticles.

Figure 6:
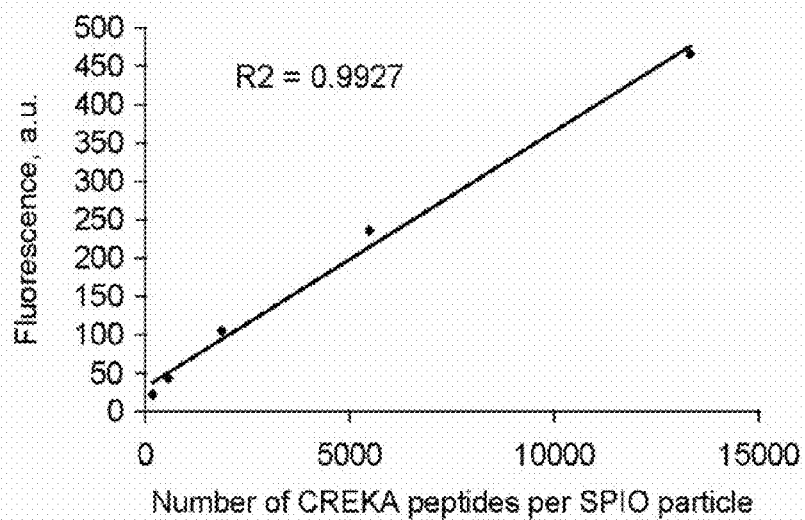
FIG. 6 shows fluorescence intensity of iron oxide nanoparticles (CREKA-SPIO) coupled to various levels of substitution with fluorescein-labeled CREKA peptide. Fluorescence emitted by the conjugated particles is linearly related to the level of substitution. A.U.=Arbitrary Units.

Fluorescein-labeled CREKA or fluorescein was coupled onto the surface of 50 nm superparamagnetic, amino dextran-coated iron oxide (SPIO) nanoparticles. Such particles have been extensively characterized with regard to their chemistry, pharmacokinetics, and toxicology, and are used as MRI contrast agents (Jung 1995; Jung 1995; Weissleder 1989). Coupling of the fluorescein-labeled peptides to SPIO produced strongly fluorescent particles. Releasing the peptide from the particles by hydrolysis increased the fluorescence further by a factor of about 3. These results indicate that the proximity of the fluorescein molecules at the particle surface causes some quenching of the fluorescence. Despite this, fluorescence from the coupled fluorescein peptide was almost linearly related to the number of peptide molecules on the particle (FIG. 6), allowing for the tracking of the number of peptide moieties on the particle by measuring particle fluorescence, and the use of fluorescence intensity as a measure of the concentration of particles in samples. CREKA-SPIO was used with at least 8,000 peptide molecules per particle in the in vivo experiments. The CREKA-SPIO nanoparticles bound to mouse and human plasma clots in vitro, and the binding was inhibited by the free peptide (FIG. 1D), The nanoparticles distributed along a fibrillar meshwork in the clots (inset in FIG. 1D). These results show that the particle-bound peptide retains its binding activity toward clotted plasma proteins.

Tumor Homing Versus Liver Clearance of CREKA-SPIO.

Figure 2:
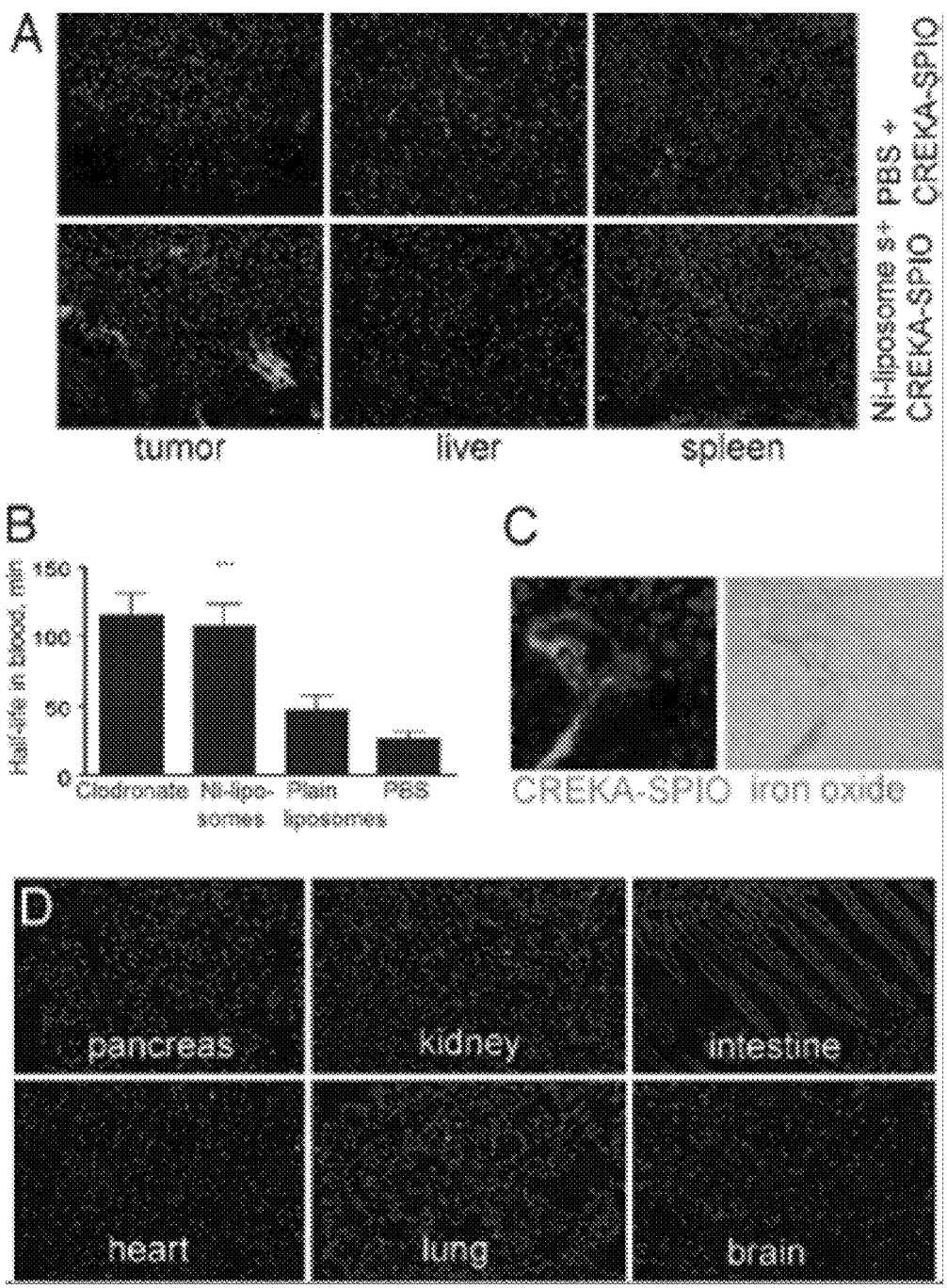
FIG. 2 shows tumor homing of CREKA-conjugated iron oxide particles. CREKA-SPIO particles were intravenously injected (4 mg Fe/kg) into Balb/c nude mice bearing MDA-MB-435 human breast cancer xenograft tumors measuring 1-1.5 cm in diameter. The mice were sacrificed by perfusion 5-6 hours later and tissues were examined for CREKA-SPIO fluorescence (green). Nuclei were stained with DAPI (blue). (A) Distribution of CREKA-SPIO in tissues from MDA-MB-435 tumor mice that received 2 hours earlier an injection of PBS (A, upper panels) or Ni/DSPC/CHOL liposomes (Ni-liposomes) containing 0.2 μmol Ni in 200 μl of PBS (A, lower panels). (B) Plasma circulation half-life of CREKA-SPIO following different treatments. At least 4 time points were collected. Data were fitted to mono-exponential decay using Prizm software (GraphPad, San Diego, Calif.), and the half-life values were compared in unpaired t-test (***$p<0.0001$, n=10). (C) Accumulation of CREKA-SPIO nanoparticles in tumor vessels. Mice were injected and tissues collected as in panel A. Fluorescent intravascular CREKA-SPIO particles overlap with iron oxide viewed in transmitted light. Magnification: 600×. (D) Control organs of Ni-liposome/CREKA-SPIO-injected mice. Occasional spots of fluorescence are seen in the kidneys and lungs. The fluorescence seen in the heart did not differ from uninjected controls, indicating that it is autofluorescence. Representative results from at least 3 independent experiments are shown. Magnification A and D, 200×; C, 600×.

Initial experiments showed that intravenously injected CREKA-SPIO nanoparticles did not accumulate effectively in MDA-MB-435 breast cancer xenografts. In contrast, a high concentration of particles was seen in reticuloendothelial system (RES) tissues (FIG. 2A, upper panels). As the free CREKA peptide effectively homes to these tumors (FIG. 5), it was hypothesized that the RES uptake was a major obstacle to the homing of the nanoparticles. The role of the RES in the clearance of CREKA-SPIO was confirmed by depleting RES macrophages in the liver with liposomal clodronate (Van Rooijen 1994). This treatment caused about a 5-fold prolongation in particle half-life (FIG. 2B). Particulate material was eliminated from the circulation because certain plasma proteins bind to the particles and mediate their uptake by the RES (opsonization; Moghimi 2001; Moore 1997). Injecting decoy particles that eliminate plasma opsonins is another commonly used way of blocking RES uptake (Souhami 1981; Fernandez-Urrusuno 1996). Liposomes coated with chelated $Ni^{2+}$ were tested as a potential decoy particle because it was surmised that iron oxide and $Ni^{2+}$ would attract similar plasma opsonins, and Ni-liposomes could therefore deplete them from the systemic circulation. Indeed, SDS-PAGE analysis showed that significantly less plasma protein bound to SPIO in the blood of mice that had been pre-treated with Ni-liposomes.

Intravenously injected Ni-liposomes prolonged the half-life of the SPIO and CREKA-SPIO in the blood by a factor of about 5 (FIG. 2B). The Ni-liposome pretreatment whether done 5 min or 48 h prior to the injection of CREKA-SPIO, greatly increased the tumor homing of the nanoparticles, which primarily localized in tumor blood vessels (FIG. 2A lower tumor panel and FIG. 2D). The local concentration of particles was so high that the brownish color of iron oxide was visible in the optical microscope (FIG. 2C, right panel), indicating that the fluorescent signal observed in tumor vessels was from intact CREKA-SPIO. Fewer particles were seen in the liver after the Ni-liposome pre-treatment, but accumulation in the spleen was unchanged or even enhanced (FIG. 2A). Other organs contained minor amounts of CREKA-SPIO particles or no particles at all, whether Ni-liposomes were used or not (FIG. 1D). Plain liposomes were tested as decoy particles. These liposomes prolonged the blood half-life and tumor homing of subsequently injected CKEKA-SPIO (FIG. 2B), showing the existence of a common clearance mechanism for liposomes and SPIO.

Nanoparticle-Induced Blood Clotting in Tumor Vessels.

Figure 3:
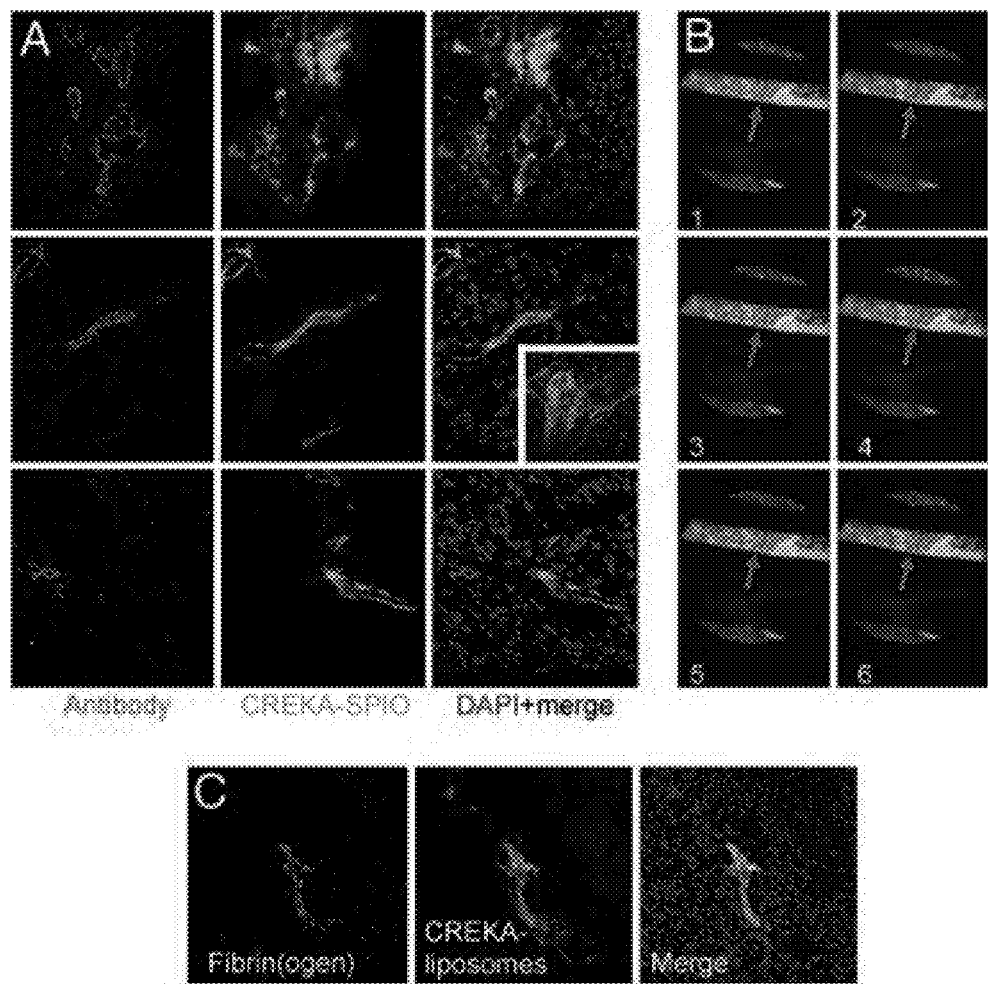
FIG. 3 shows the accumulation of CREKA-SPIO nanoparticles in tumor vessels. Mice bearing MDA-MB-435 xenografts were injected with Ni-liposomes and CREKA-SPIO nanoparticles as described in the legend to FIG. 2. The mice were perfused 6 hours after the nanoparticle injection and tissues were collected. (A) Upper panels: Co-localization of nanoparticle fluorescence with CD31 staining in blood vessels; Middle panels: Co-localization of nanoparticle fluorescence and anti-fibrin(ogen) staining in tumor blood vessels. Inset—an image showing CREKA-SPIO distributed along fibrils in a tumor blood vessel; Lower panels: Lack of co-localization of nanoparticle fluorescence with anti-CD41 staining for platelets. (B) Intravital confocal microscopy of tumors using DiI-stained red blood cells as a marker of blood flow. The arrow points to a vessel in which stationary erythrocytes indicate obstruction of blood flow. Blood flow in the vessel above is not obstructed. Six successive frames from a 1-min movie (Movie 2 in Supplementary Material) are shown. (C) CREKA-coated liposomes co-localize with fibrin in tumor vessels. The results are representative of 3 independent experiments. Magnification: A and C, 600×, B, 200×.

CREKA-SPIO particles administered after liposome pre-treatment primarily colocalized with tumor blood vessels, with some particles appearing to have extravasated into the surrounding tissue (FIG. 3A, top panels). Significantly, up to 20% of tumor vessel lumens were filled with fluorescent masses. These structures stained for fibrin (FIG. 3A, middle panels), showing that they are blood clots impregnated with nanoparticles. In some of the blood vessels the CREKA-SPIO nanoparticles were distributed along a meshwork (inset), possibly formed of fibrin and associated proteins, and similar to the pattern shown in the inset of FIG. 1D.

Figure 7:
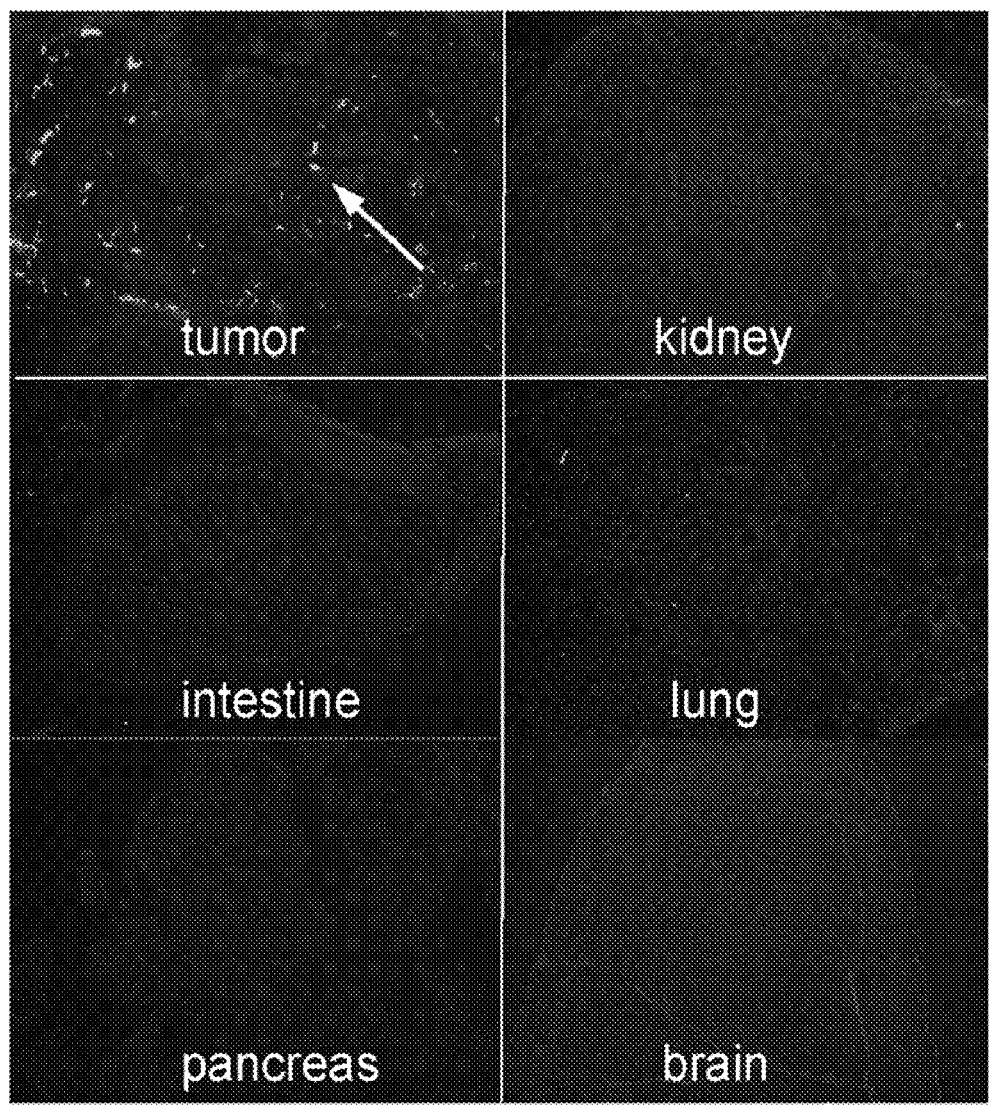
FIG. 7 shows CREKA-SPIO nanoparticles accumulate in tumor tissue, but not in non-RES normal tissues. The low magnification (40×) was used to produce these images because only blood vessels in which clotting had concentrated the CREKA-SPIO fluorescence are visible at this magnification. Note the entrapment of nanoparticles in clots in tumor tissue (arrow), but not in non-RES normal tissues. The injections were carried out and the tissues prepared for analysis as in FIG. 2. A representative experiment out of 10 is shown.
Figure 8:
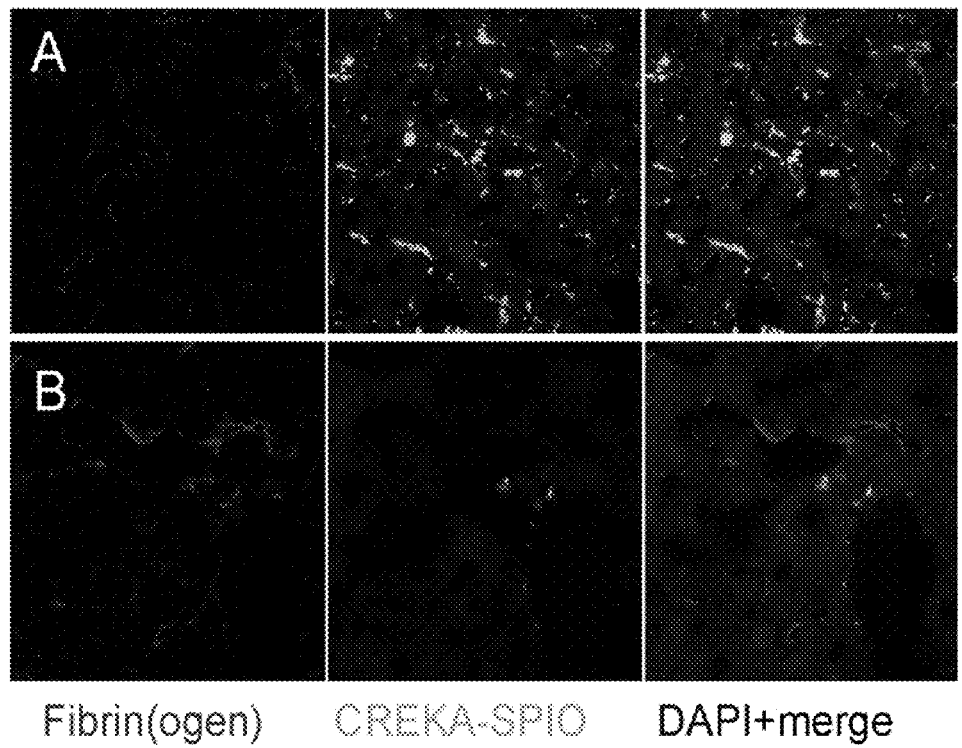
FIG. 8 shows lack of colocalization of fibrin(ogen) staining and CREKA-SPIO in the liver. The fibrin(ogen)-positive structures can be background from fibrinogen production by the liver, as it does not co-localize with the nanoparticles (A), and the liver from a non-injected mouse showed similar fibrin (ogen) staining (B). Magnification 600×.

Among the non-RES tissues, the kidneys and lungs contained minor amounts of specific CREKA-SPIO fluorescence (FIG. 2D). However, low magnification images, which reveal only blood vessels with clots in them, showed no clotting in these tissues, with the exception of very rare clots in the kidneys (FIG. 7). Despite massive accumulation of nanoparticles in the liver no colocalization between fibrin(ogen) staining and CREKA-SPIO fluorescence in liver vessels (FIG. 8) was seen. Moreover, liver tissue from a non-injected mouse also stained for fibrin(ogen) (FIG. 8B), presumably reflecting fibrinogen production by hepatocytes. Thus, the clotting induced by CREKA-SPIO nanoparticles is essentially confined to tumor vessels.

Figure 9:
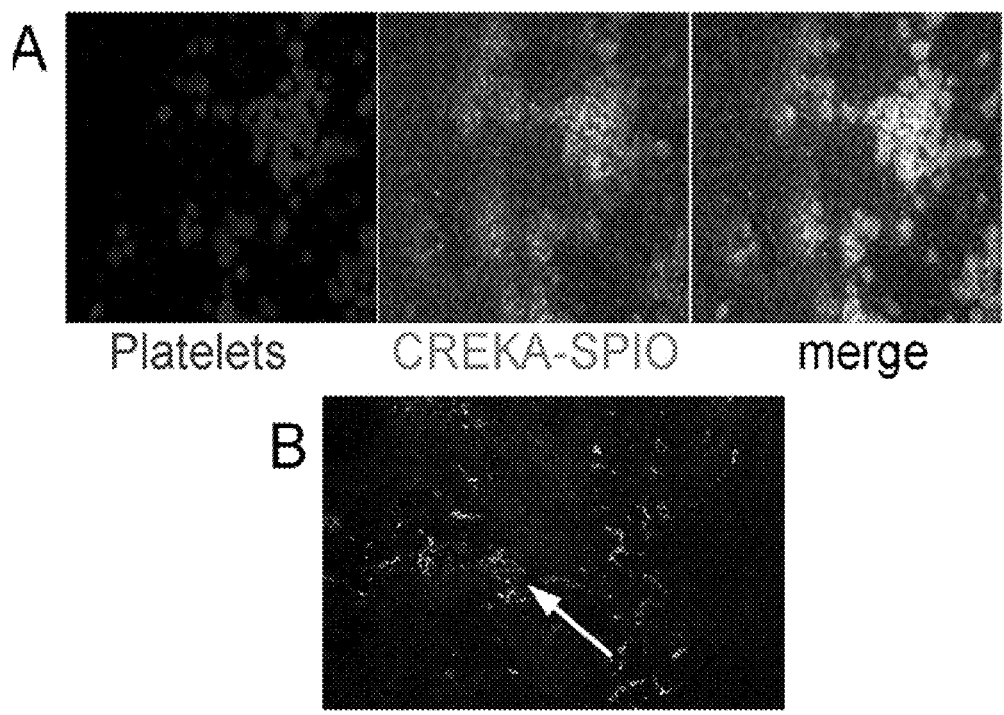
FIG. 9 shows the role of platelets in nanoparticle homing. (A). Blood was drawn 5 min post-injection of 4 mg/kg of CREKA-SPIO into mice and a 50 μl aliquot was run through a magnetic column. Bound CREKA-SPIO particles were eluted form the column, concentrated on a slide, and stained with anti-CD41 antibody. Some of the particles appear to be associated with platelets. (B). A low-magnification image (40×) showing CREKA-SPIO homing and clot formation in a tumor from a platelet-depleted mouse. Platelet depletion was accomplished by treating mice with 0.1 mg of an anti-CD41 monoclonal antibody as described (Van der Heyde and Gramaglia (2005)). The mice subsequently received Ni-liposomes/CREKA-SPIO as described in the legend of FIG. 2. The anti-platelet treatment did not decrease the incidence of fluorescent clots (compare with the tumor panel in FIG. 7).

Nanoparticles can cause platelet activation and enhance thrombogenesis (Radomski 2005; Khandoga 2004). Some CREKA-SPIO nanoparticles (<1%) recovered from blood were associated with platelets (FIG. 9A), but staining for a platelet marker showed no colocalization between the platelets and CREKA-SPIO nanoparticles in tumor vessels (FIG. 3A, lower panels). Thrombocytopenia was also induced by injecting mice with an anti-CD41 monoclonal antibody (Van der Heyde 2005) and no noticeable effect on CREKA-SPIO homing to the MDA-MB-435 tumors was found (FIG. 9B). These results indicate that platelets are not involved in the homing pattern of CREKA-SPIO.

The deep infiltration of clots by nanoparticles showed that these clots must have formed at the time particles were circulating in blood, rather than before the injection. This was tested with intravital confocal microscopy, using DiI-labeled erythrocytes as a flow marker. There was time-dependent clot formation and obstruction of blood flow in tumor blood vessels with parallel entrapment of CREKA-SPIO in the forming clots (FIG. 3B).

It was next tested whether the clotting-inducing effect was specific for SPIO particles, or could be induced with a different CREKA-coated particle. Liposomes into which fluorescein-CREKA peptide was incorporated that was coupled to lipid-tailed polyethylene glycol (PEG) was used. Like CREKA-SPIO, the CREKA-liposomes selectively homed to tumors and co-localized with fibrin within tumor vessels (FIG. 3C), showing that CREKA liposomes are also capable of causing clotting in tumor vessels. No clotting was seen when control SPIO or control liposomes were injected in the tumor mice.

Clotting-Amplified Tumor Targeting.

The contribution of clotting to the accumulation of CREKA-SPIO in tumor vessels was also studied. Quantitative analysis of tumor magnetization with a Superconducting Quantum Interference Device (SQUID) (FIG. 4A) and measurement of the fluorescence signal revealed about 6-fold greater accumulation of CREKA-SPIO in Ni-liposome-pretreated mice compared to PBS-pretreated mice. Aminated SPIO control particles did not significantly accumulate in the tumors (FIG. 4A).

Figure 4:
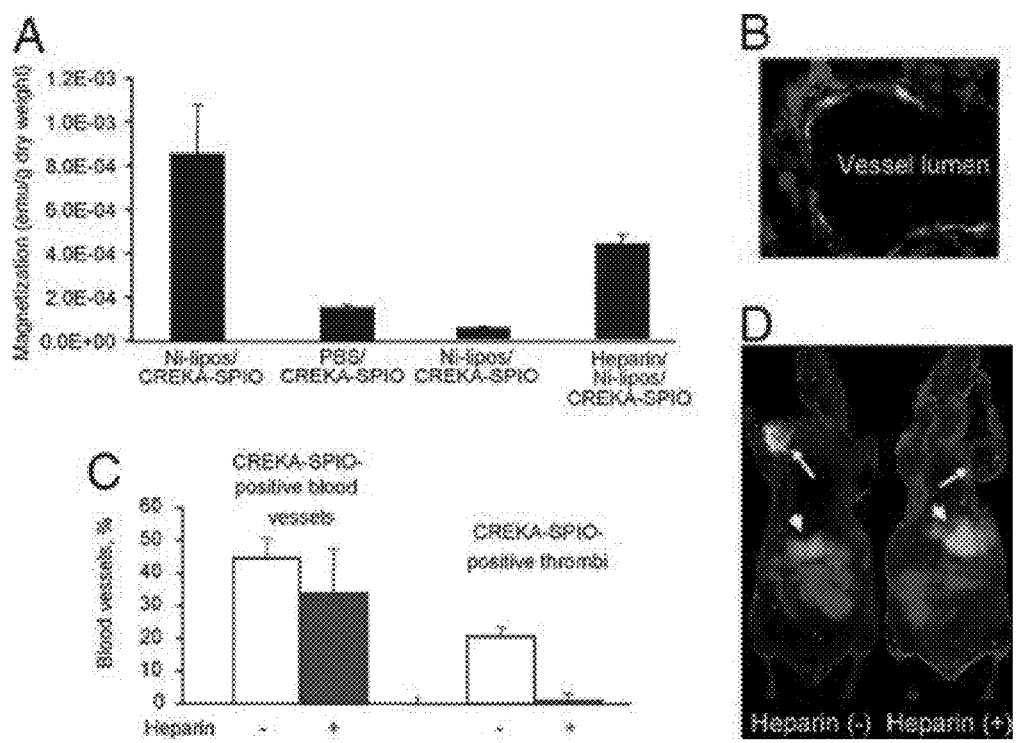
FIG. 4 shows the effect of blood clotting on nanoparticle accumulation in tumors. Mice bearing MDA-MB-435 human breast cancer xenografts were intravenously injected with PBS or a bolus of 800 U/kg of heparin followed 120 min later by Ni-liposomes (or PBS) and CREKA-SPIO (or control nanoparticles). The mice received additional heparin by intraperitoneal injections (a total of 1000 U/kg) or PBS throughout the experiment. (A) Tumors were removed 6 hours after the nanoparticle injection, and magnetic signal in the tumor after different treatments was determined with SQUID. Aminated dextran SPIO served as a particle control (control SPIO). SPIO nanoparticle concentration in tissues is represented by the saturation magnetization value (electromagnetic unit, emu) of the tissue at 1 T magnetic field after the subtraction of the diamagnetic and the paramagnetic background of blank tissue. The magnetization values were normalized to dry weight of the tissue. Results from 3 experiments are shown. (B) Quantification of heparin effect on clotting in blood vessels. Mice were pretreated with PBS (white bars) or heparin (black bars) as described above, followed by Ni liposomes/CREKA-SPIO nanoparticles. Three sections from two tumors representing each treatment were stained with anti-CD31 for blood vessels, and the percentage of vessels positive for fluorescence and fluorescent clots was determined. Note that heparin did not significantly change the percentage of blood vessels containing particles, but dramatically decreased the incidence of the lumens that are filled with fluorescence. (C) A representative example of the appearance of CREKA-SPIO particles in tumor vessels of mice treated with heparin. (D) Near-infrared imaging of mice that received Ni-liposomes followed by Cy7-labeled CREKA-SPIO with or without heparin pretreatment. The images were acquired 8 hours after the injection of the CREKA-SPIO particles using an Odyssey 2 NIR scanner (Li-COR Biosciences, Lincoln, Nebr.). The images shown are composites of 2 colors, red (700 nm channel, body and chow autofluorescence) and green (800 nm channel, Cy7). Arrows point to the tumors, arrowheads to the liver. Note the strong decrease in signal from the tumor in the heparin-pretreated mouse. A representative experiment out of 3 is shown.

The SQUID measurements revealed that injecting heparin, which is a strong clotting inhibitor, prior to injection of CREKA-SPIO, reduced tumor accumulation of nanoparticles by more than 50% (FIG. 4A). Microscopy showed that heparin reduced the fibrin-positive/CREKA-SPIO positive structures within tumor vessels, but that the particles still bound along the walls of the vessels, presumably to preexisting fibrin deposits (a representative image is shown in FIG. 4B). Separate quantification of the homing pattern showed that heparin did not significantly reduce the number of vessels with nanoparticles bound to the vessel walls, but essentially eliminated the intravascular clotting (FIG. 4C). Thus, the binding of CREKA-SPIO to tumor vessels does not require the clotting activity that is associated with these particles, but clotting improves the efficiency of the tumor homing.

The clotting induced by CREKA-SPIO caused a particularly strong enhancement of tumor signal in whole-body scans. CREKA-SPIO nanoparticles labeled with Cy7, a near infrared fluorescent compound, effectively accumulated in tumors (FIG. 4D, image on the left, arrow), with a significant signal from the liver as well (arrowhead). The reduction in the tumor signal obtained with heparin (FIG. 4D, image on the right) appeared greater in the fluorescence measurements than the 50% value determined by SQUID, possibly because the concentrated signal from the clots enhanced optical detection of the fluorescence. These results show that the clotting induced by CREKA-SPIO provides a particular advantage in tumor imaging.

ii. Discussion

This example describes an example of a nanoparticle system that provides effective accumulation of the particles in tumors. The system is based on four elements: First, coating of the nanoparticles with a tumor-homing peptide that binds to clotted plasma proteins endows the particles with a specific affinity for tumor vessels (and tumor stroma). Second, decoy particle pretreatment prolongs the blood half-life of the particles and increases tumor targeting. Third, the tumor-targeted nanoparticles cause intravascular clotting in tumor blood vessels. Fourth, the intravascular clots attract more nanoparticles into the tumor, amplifying the targeting.

A peptide with specific affinity for clotted plasma proteins was chosen as the targeting element for the nanoparticles. The interstitial spaces of tumors contain fibrin and proteins that become cross-linked to fibrin in blood clotting, such as fibronectin (Dvorak 1985; Pilch 2006). The presence of these products in tumors, but not in normal tissues, can be a result of leakiness of tumor vessels, which allows plasma proteins to enter from the blood into tumor tissue, where the leaked fibrinogen is converted to fibrin by tissue procoagulant factors (Dvorak 1985; Abe 1999). The clotting creates new binding sites that can be identified and accessed with synthetic peptides (Pilch 2006). The present results show that the CREKA-modified nanoparticles not only bind to blood and plasma clots, but can also induce localized tumor clotting. The nature of the particle is not limited for this activity, as it was found that both CREKA-coated iron oxide and micron-sized CREKA-coated liposomes cause clotting in tumor vessels. The binding of one or more clotting products by the CREKA-modified particles can shift the balance of clotting and clot dissolution in the direction of clot formation, and the presence of this activity at the surface of particles can facilitate contact-dependent coagulation.

Some nanomaterials are capable of triggering systemic thrombosis (Gorbet 2004), but here the thrombosis induced by the CREKA particles was confined to tumor vessels. The high concentration of the targeted particles in tumor vessels can explain the selective localization of the thrombosis to tumor vessels. However, since no detectable clotting was seen in the liver, where the nanoparticles also accumulate at high concentrations, other factors must be important. The procoagulant environment common in tumors can be a major factor contributing to the tumor specificity of the clotting (Boccaccio 2005).

A major advantage of nanoparticles is that multiple functions can be incorporated onto a single entity. Described herein is an in vivo function for nanoparticles; self-amplifying tumor homing enabled by nanoparticle-induced clotting in tumor vessels and the binding of additional nanoparticles to the clots. This nanoparticle system combines several other functions into one particle: specific tumor homing, avoidance of the RES, and effective tumor imaging. Optical imaging was used in this work, but the IO platform also enables MRI imaging. The clotting caused by CREKA-SPIO nanoparticles in tumor vessels serves to focally concentrate the particles in a manner that appears to improve tumor detection by microscopic and whole-body imaging techniques.

Another function of the targeted particles is that they cause physical blockade of tumor vessels by local embolism. Blood vessel occlusion by embolism or clotting can reduce tumor growth (Huang 1997; El-Sheikh 2005). To date, a 20% occlusion rate in tumor vessels has been achieved. Due to the modular nature of nanoparticle design, the functions described herein can be incorporated into particles with additional activities. Drug-carrying nanoparticles that accumulate in tumor vessels and slowly release the drug payload while simultaneously occluding the vessels can be used with the methods and compositions disclosed herein.

iii. Materials and Methods

Phage Screening, Tumors and Peptides.

In vivo screening of a peptide library with the general structure of $CX_7C$ (SEQ ID NO: 4), where C is cysteine and X is any amino acid, was carried out as described (Oh 2004) using 65- to 75-day-old transgenic MMTV PyMT mice (Hutchinson 2000). These mice express the polyoma virus middle T antigen (MT) under the transcriptional control of the mouse mammary tumor virus (MMTV), leading to the induction of multi-focal mammary tumors in 100% of carriers. MDA-MB-435 tumors in nude mice and peptide synthesis have been described (Laakkonen 2002; Laakkonen 2004). B16F1 murine melanoma tumors were grown in fibrinogen null mice (Suh 1995) and their normal littermates and used when they reached 0.5-1 cm in size (Pilch 2006).

Nanoparticles and Liposomes.

Amino group-functionalized dextran-coated superparamagnetic iron oxide nanoparticles (50 nm nanomag-D-SPIO; Micromod Partikeltechnologie GmbH, Rostock, Germany) were coupled with CREKA peptide using a crosslinker. The final coupling ratio was 30 nmol fluorescein-labeled peptide molecules per mg iron oxide, or 8,000 peptides/particle. For near-infrared labeling with Cy7, about 20% of the amines were derivatized with Cy7-NHS ester (GE Healthcare BioSciences, Piscataway, N.J.), and the remaining amines were used for conjugating the peptide. Detail on the SPIO and the preparation of liposomes are described below. Clodronate was purchased from Sigma and incorporated into liposomes as described (Van Rooijen and Sanders (1994)).

Nanoparticle Injections.

For intravenous injections, the animals were anesthetized with intraperitoneal Avertin, and liposomes (2 μmol DSPC) and/or nanoparticles (1-4 mg Fe/kg body weight) were injected into the tail vein. The animals were sacrificed 5-24 h post-injection by cardiac perfusion with PBS under anesthesia, and organs were dissected and analyzed for particle homing. To suppress liver macrophages, mice were intravenously injected with liposomal clodronate suspension (100 μl per mouse), and the mice were used for experiments 24 hours later.

Phage and Nanoparticle Binding to Clots.

Phage binding to clotted plasma proteins was determined as described (Pilch 2006). CREKA-SPIO and control SPIO were added to freshly formed plasma clots in the presence or absence of free CREKA peptide. After 10 min incubation, the clots were washed 4 times in PBS, transferred to a new tube and digested in 100 μl concentrated nitric acid. The digested material was diluted in 2 ml distilled water and the iron concentration was determined using inductively coupled plasma-optical emission spectroscopy (ICP-OES, PerkinElmer, Norwalk, Conn.).

Nanoparticle Preparation.

When necessary to achieve high peptide coupling density, additional amino groups were added to commercially obtained SPIO as follows: First, to crosslink the particles before the amination step, 3 ml of the colloid (~10 mgFe/ml in double-distilled water) was added to 5 ml of 5M NaOH and 2 ml of epichlorohydrin (Sigma, St. Louis, Mo.). The mixture was agitated for 24 hours at room temperature to promote interaction between the organic phase (epichlorohydrin) and aqueous phase (dextran-coated particle colloid). In order to remove excess epichlorohydrin, the reacted mixture was dialyzed against double-distilled water for 24 hours using a dialysis cassette (10,000 Da cutoff, Pierce, Rockford Ill.). Amino groups were added to the surface of the particles as follows: 0.02 ml of concentrated ammonium hydroxide (30%) was added to 1 ml of colloid (~10 mg Fe/ml). The mixture was agitated at room temperature for 24 hours. The reacted mixture was dialyzed against double-distilled water for 24 hours. To further rinse the particles, the colloid was trapped on a MACS® Midi magnetic separation column (Miltenyi Biotec, Auburn Calif.), rinsed with PBS three times, and eluted from the column with 1 ml PBS.

To conjugate CREKA peptide to SPIO, the particles were re-suspended at a concentration of 1 mg Fe/ml, and heterobifunctional linker N-[a-maleimidoacetoxy]succinimide ester (AMAS; Pierce) was added (2.5 mg linker per 2 mg Fe) under vortexing. After incubation at room temperature for 40 min, the particles were washed 3 times with 10 ml PBS on a MACS column. The peptide with free terminal cysteine was then added (100 μg peptide per 2 mg Fe). After incubation overnight at 4° C. the particles were washed again and re-suspended in PBS at a concentration of 0.35 mg/ml of Fe). To quantify the number of peptide molecules conjugated to the particles, a known amount of stock or AMAS-activated particles was incubated with varying amounts of the peptide. After completion of the incubation the particles were pelleted at 100.000 G using Beckman TLA 100.3 ultracentrifuge rotor (30 min) and the amount of the unbound peptide was quantified by fluorescence. To cleave the conjugated peptide from the particles, the particles were incubated at 37° C. overnight at pH 10. The concentration of free peptide in the supernatant was determined by reading fluorescence and by using the calibration curve obtained for the same peptide. The fluorescence intensity of known amounts of particles was plotted as a function of peptide conjugation density, and the slope equation was used to determine conjugation density in different batches.

Liposome Preparation.

To prepare liposomes, 1,2-Distearoyl-sn-glycero-3-phosphocholine (DSPC), cholesterol, and 1,2-Dioleoyl-sn-glycero-3-{[N(5-amino-1-carboxypentyl)iminodiacetic acid] succinyl} (nickel salt) (all from Avanti Polar Lipids, Alabaster Ala.), were mixed in chloroform at a molar ratio of 57:37:10 and evaporated in a rotary evaporator until dry. The lipids were hydrated in PBS to a final DSPC concentration 10 mM. The lipid mixture was extensively bath sonicated for 10 min at 55° C. to facilitate liposome formation. For plain liposomes only DSPC and cholesterol were used at a molar ratio of 57:37.

CREKA-decorated liposomes were prepared by reacting PEG-DSPE-maleimide (Avanti) with a 2-fold molar excess of CREKA. The reaction was performed at room temperature under nitrogen in PBS buffer, pH 7.4. After the reaction had been completed in 2 hours, the product (yellow precipitate) was washed by centrifugation and dissolved in ethanol. The ethanol solution was stored at −20° C. CREKA-PEG was incorporated by adding a liposome suspension to a dried film of CREKA-PEG-DSPE, heating to 55° C. while vortexing for 1 hour. Control liposomes were prepared as above but using FITC-PEG-DSPE instead. The liposome preparations were kept at 4° C. until used.

Analysis of Protein Binding by Nanoparticles.

To test the binding of soluble plasma proteins to SPIO nanoparticles, the particles were incubated with citrated mouse plasma at a concentration of 1-2 mg iron/ml plasma. Alternatively, the particles were injected into animals and plasma was collected 5-10 min post-injection. The particles were washed on the magnetic column to remove non-bound proteins, and the particles were boiled in 10% SDS for 20 min. The iron oxide was pelleted by ultracentrifugation (100.000 g, 10 min) and the eluted proteins in the supernatant were precipitated with acetone overnight at −20° C. The protein pellet was analyzed by SDS-PAGE, and the gels were silver stained (SilverQuest, Invitrogen, Carlsbad, Calif.). For mass spectrometric analysis, proteins extracted from the particles were reconstituted in water; a protein aliquot was digested with trypsin and analyzed using Applied Biosystems PE SCIEX QSTARR liquid chromatograph Q-TOF mass spectrometer, Foster City, Calif. The data were analyzed using Mascot search engine (Matrix Science, Boston, Mass.).

Nanoparticle Clearance.

Heparinized capillaries were used to draw 50 μl of blood from the periorbital plexus at different times after nanoparticle injection, the blood was centrifuged at 300 g for 2 min, and a 10 μl aliquot of platelet-rich plasma was diluted into 600 μl 1M Tris solution, pH 8.4. Fluorescence was determined on a PerkinElmer (Norwalk, Conn.) LS50B spectrofluorometer, and plotted as a function of the time the particles had circulated.

Intravital Microscopy.

Tumor blood flow in MDA-MB 435 xenograft-bearing mice was observed by intravital microscopy. Mice were pre-injected with Ni-liposomes and $5 \times 10^8$ of DiI-labeled erythrocytes. A skin flap was moved aside to expose the tumors, and the mice were intravenously injected with 4 mg/kg of fluorescein-CREKA-SPIO (time "0"). The tumors were scanned with IV-100 intravital laser scanning microscope (Olympus Corp., Tokyo, Japan) using an IV-OB35F22W29 MicroProbe objective (Olympus Corp., Tokyo, Japan). Movies were recorded at 10 min intervals up to 120 min post-injection.

Magnetic Measurements of the Tissue Samples Using Superconducting Quantum Interference Device (SQUID) Magnetometer.

Tissue samples were frozen immediately upon collection, lyophilized, weighed, and placed in gelatin capsules. The capsules were inserted into the middle of transparent plastic straws for magnetic measurements made using a Quantum Design MPMS2 SQUID magnetometer (San Diego, Calif.) operated at 150 K. The samples were exposed to direct current magnetic fields in stepwise increments up to one Tesla. Corrections were made for the diamagnetic contribution of tissue, capsule and straw.

REFERENCES

1. Desai N, Trieu V, Yao Z, Louie L, Ci S, Yang A, Tao C, De T, Beals B, Dykes D, Noker P, Yao R, Labao E, Hawkins M, Soon-Shiong P (2006) *Clin Cancer Res* 12: 1317-1324.
2. Weissleder R, Bogdanov A, Jr, Neuwelt E A, Papisov M (1995) *Advanced Drug Delivery Reviews* 16: 321-334.
3. Sinek J, Frieboes H, Zheng X, Cristini V (2004) *Biomed Microdevices* 6: 297-309.
4. Boucher Y, Baxter L T, Jain, R K (1990) *Cancer Res* 50: 4478-4484.
5. Hoffman J A, Giraudo E, Singh M, Zhang L, Inoue M, Porkka K, Hanahan D, Ruoslahti E (2003) *Cancer Cell* 4: 383-391.
6. Oh P, Li Y, Yu J, Durr E, Krasinska K M, Carver L A, Testa J E, Schnitzer J E (2004) *Nature* 429: 629-635.
7. Ruoslahti, E (2002) *Nat Rev Cancer* 2: 83-90.
8. DeNardo S J, DeNardo G L, Miers L A, Natarajan A, Foreman A R, Gruettner C, Adamson G N, Ivkov R (2005) *Clin Cancer Res* 11: 7087s-7092s.
9. Akerman M E, Chan W C, Laakkonen P, Bhatia S N, Ruoslahti E (2002) *Proc Natl Acad Sci USA* 99: 12617-12621.
10. Cai W, Shin D W, Chen K, Gheysens O, Cao Q, Wang S X, Gambhir S S, Chen X (2006) *Nano Lett* 6: 669-676.
11. Pasqualini R, Ruoslahti E (1996) *Nature* 380: 364-366.
12. Hutchinson J N, Muller W J (2000) *Oncogene* 19: 6130-6137.
13. Dvorak H F, Senger D R, Dvorak A M, Harvey V S, McDonagh J (1985) *Science* 227: 1059-1061.

14. Abe K, Shoji M, Chen J, Bierhaus A, Danave I, Micko C, Casper K, Dillehay D L, Nawroth P P, Rickles F R (1999) *Proc Natl Acad Sci USA* 96: 8663-8668.
15. Pilch J, Brown D M, Komatsu M, Jarvinen T A, Yang M, Peters D, Hoffman R M, Ruoslahti E (2006) *Proc Natl Acad Sci USA* 103: 2800-2804.
16. Jung C W, Jacobs P (1995) *Magn Reson Imaging* 13: 661-674.
17. Jung, C W (1995) *Magn Reson Imaging* 13: 675-691.
18. Weissleder R, Stark, D D, Engelstad B L, Bacon B R, Compton C C, White D L, Jacobs P, Lewis J (1989) *AJR Am J Roentgenol* 152: 167-173.
19. Van Rooijen N, Sanders A (1994) *J Immunol Methods* 174: 83-93.
20. Moghimi S M, Hunter A C, Murray J C (2001) *Pharmacol Rev* 53: 283-318.
21. Moore A, Weissleder R, Bogdanov A, Jr (1997) *J Magn Reson Imaging* 7: 1140-1145.
22. Souhami R L, Patel H M, Ryman B E (1981) *Biochim Biophys Acta* 674: 354-371.
23. Fernandez-Urrusuno R, Fattal E, Rodrigues J M, Jr, Feger J, Bedossa P, Couvreur P (1996) *J Biomed Mater Res* 31: 401-408.
24. Radomski A, Jurasz P, Alonso-Escolano D, Drews M, Morandi M, Malinski T, Radomski M W (2005) *Br J Pharmacol* 146: 882-93.
25. Khandoga A, Stampfl A, Takenaka S, Schulz H, Radykewicz R, Kreyling W, Krombach F (2004) *Circulation* 109: 1320-1325.
26. Van der Heyde H C, Gramaglia I, Sun G, Woods C (2005) *Blood* 105: 1956-1963.
27. Gorbet M B, Sefton M V (2004) *Biomaterials* 25: 5681-5703.
28. Boccaccio C, Sabatino G, Medico E, Girolami F, Follenzi A, Reato G, Sottile A, Naldini L, Comoglio P M (2005) *Nature* 434: 396-400.
29. Huang X, Molema G, King S, Watkins L, Edgington T S, Thorpe P E (1997) *Science* 275: 547-550.
30. El-Sheikh A, Borgstrom P, Bhattacharjee G, Belting M, Edgington T S (2005) *Cancer Res* 65: 11109-11117.
31. Hutchinson J N, Muller W J (2000) *Oncogene* 19: 6130-6137.
32. Laakkonen P, Porkka K, Hoffman J A, Ruoslahti E (2002) *Nat Med* 8: 751-755.
33. Laakkonen P, Akerman M E, Biliran H, Yang M, Ferrer F, Karpanen T, Hoffman R M, Ruoslahti E (2004) *Proc Natl Acad Sci USA* 101: 9381-9386.
34. Suh T T, Holmback K, Jensen N J, Daugherty C C, Small K, Simon D I, Potter S, Degen J L (1995) *Genes Dev* 9: 2020-2033
35. Van Rooijen N, Sanders A (1994) *J Immunol Methods* 174: 83-93.

| Sequences | |
|---|---|
| CREKA | SEQ ID NO: 1 |
| CGLIIQKNEC | SEQ ID NO: 2 |
| CNAGESSKNC | SEQ ID NO: 3 |
| CXXXXXXXC, | SEQ ID NO: 4 | where C is cysteine and X is any amino acid

---

We claim:

1. A conjugate comprising a surface molecule and a plurality of clot binding compounds conjugated to the surface molecule, wherein the clot binding compounds selectively bind to clotted plasma protein, wherein the conjugate causes clotting and amplifies the accumulation of the conjugate in tumors, wherein some of the plurality of the clot binding compounds each independently comprise an amino acid segment comprising the amino acid sequence REK, wherein the surface molecule is an iron oxide nanoparticle.

2. The conjugate of claim 1, wherein all of the plurality of clot binding compounds each independently comprise an amino acid segment comprising the amino acid sequence REK.

3. The conjugate of claim 1, wherein the amino acid segments each independently comprise the amino acid sequence CREKA (SEQ ID NO: 1).

4. The conjugate of claim 3, wherein the amino acid segment consists of the amino acid sequence CREKA (SEQ ID NO: 1).

5. The conjugate of claim 1, wherein sufficiency of the density and composition of clot binding compounds is determined by assessing clotting and amplification of the accumulation of the conjugate in tumors in a non-human animal.

6. The conjugate of claim 1, wherein some of the plurality of clot binding compounds are each independently selected from an amino acid segment comprising a fibrin-binding peptide, a clot binding antibody, and a clot binding small organic molecule.

7. The conjugate of claim 1, wherein the amino acid segments are each independently selected from amino acid segments comprising the amino acid sequence CREKA (SEQ ID NO: 1), amino acid segments consisting of the amino acid sequence CREKA (SEQ ID NO: 1), and amino acid segments consisting of the amino acid sequence REK.

8. The conjugate of claim 1, wherein the amino acid segment consists of the amino acid sequence CREKA (SEQ ID NO: 1).

9. The conjugate of claim 1, wherein some of the plurality of clot binding compounds each comprise a fibrin-binding peptide.

10. The conjugate of claim 9, wherein the fibrin-binding peptides are independently selected from the group consisting of fibrin binding peptides and fibrin-binding derivatives thereof.

11. The conjugate of claim 1, wherein the conjugate comprises at least 100 clot binding compounds.

12. The conjugate of claim 1, wherein the conjugate comprises at least 1000 clot binding compounds.

13. The conjugate of claim 1, wherein the conjugate comprises at least 1200 clot binding compounds.

14. The conjugate of claim 1, wherein the conjugate comprises at least 1500 clot binding compounds.

15. The conjugate of claim 1, wherein the conjugate comprises at least 2000 clot binding compounds.

16. The conjugate of claim 1, wherein the conjugate comprises at least 10,000 clot binding compounds.

17. The conjugate of claim 1, wherein conjugate further comprises one or more moieties, each of the one or more moieties being independently selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a detectable agent, a fluorophore, fluorescein, rhodamine, a radionuclide, indium-111, technetium-99, carbon-11, and carbon-13.

18. The conjugate of claim 17, wherein at least one of the moieties is a therapeutic agent.

19. The conjugate of claim 18, wherein the therapeutic agent is paclitaxel.

20. The conjugate of claim 18, wherein the therapeutic agent is taxol.

21. The conjugate of claims 17, wherein at least one of the moieties is a detectable agent.

22. The conjugate of claim 1, wherein the conjugate selectively homes to clotted plasma protein.

23. The conjugate of claim 1, wherein the conjugate selectively homes to tumor vasculature, wound sites, or both.

24. The conjugate of claim 1, wherein clotted plasma protein comprises fibrin.

25. A conjugate comprising a surface molecule and a plurality of clot binding compounds conjugated to the surface molecule, wherein the clot binding compounds selectively bind to clotted plasma protein, wherein the conjugate causes clotting and amplifies the accumulation of the conjugate in tumors, wherein some of the plurality of the clot binding compounds each independently comprise an amino acid segment comprising the amino acid sequence CREKA (SEQ ID NO: 1), wherein the surface molecule is an iron oxide nanoparticle.

26. The conjugate of claim 25, wherein all of the plurality of clot binding compounds each independently comprise an amino acid segment comprising the amino acid sequence REK.

27. The conjugate of claim 25, wherein the amino acid segments each independently comprise the amino acid sequence CREKA (SEQ ID NO: 1).

28. The conjugate of claim 27, wherein the amino acid segment consists of the amino acid sequence CREKA (SEQ ID NO: 1).

29. The conjugate of claim 25, wherein sufficiency of the density and composition of clot binding compounds is determined by assessing clotting and amplification of the accumulation of the conjugate in tumors in a non-human animal.

30. The conjugate of claim 25, wherein some of the plurality of clot binding compounds are each independently selected from an amino acid segment comprising a fibrin-binding peptide, a clot binding antibody, and a clot binding small organic molecule.

31. The conjugate of claim 25, wherein the amino acid segments are each independently selected from amino acid segments comprising the amino acid sequence CREKA (SEQ ID NO: 1), amino acid segments consisting of the amino acid sequence CREKA (SEQ ID NO: 1), and amino acid segments consisting of the amino acid sequence REK.

32. The conjugate of claim 25, wherein the amino acid segment consists of the amino acid sequence CREKA (SEQ ID NO: 1).

33. The conjugate of claim 25, wherein some of the plurality of clot binding compounds each comprise a fibrin-binding peptide.

34. The conjugate of claim 33, wherein the fibrin-binding peptides are independently selected from the group consisting of fibrin binding peptides and fibrin-binding derivatives thereof.

35. The conjugate of claim 25, wherein the conjugate comprises at least 100 clot binding compounds.

36. The conjugate of claim 25, wherein the conjugate comprises at least 1000 clot binding compounds.

37. The conjugate of claim 25, wherein the conjugate comprises at least 1200 clot binding compounds.

38. The conjugate of claim 25, wherein the conjugate comprises at least 1500 clot binding compounds.

39. The conjugate of claim 25, wherein the conjugate comprises at least 2000 clot binding compounds.

40. The conjugate of claim 25, wherein the conjugate comprises at least 10,000 clot binding compounds.

41. The conjugate of claim 25, wherein conjugate further comprises one or more moieties, each of the one or more moieties being independently selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a detectable agent, a fluorophore, fluorescein, rhodamine, a radionuclide, indium-111, technetium-99, carbon-11, and carbon-13.

42. The conjugate of claim 41, wherein at least one of the moieties is a therapeutic agent.

43. The conjugate of claim 42, wherein the therapeutic agent is paclitaxel.

44. The conjugate of claim 42, wherein the therapeutic agent is taxol.

45. The conjugate of claims 41, wherein at least one of the moieties is a detectable agent.

46. The conjugate of claim 25, wherein the conjugate selectively homes to clotted plasma protein.

47. The conjugate of claim 25, wherein the conjugate selectively homes to tumor vasculature, wound sites, or both.

48. The conjugate of claim 25, wherein clotted plasma protein comprises fibrin.

* * * * *